US007940396B2

(12) United States Patent
Nisper et al.

(10) Patent No.: US 7,940,396 B2
(45) Date of Patent: *May 10, 2011

(54) MEASURING AN APPEARANCE PROPERTY OF A SURFACE USING A SPATIALLY UNDER-SAMPLED BIDIRECTIONAL REFLECTANCE DISTRIBUTION FUNCTION

(75) Inventors: Jon Kenneth Nisper, Grand Rapids, MI (US); Patrick S. Rood, Walker, MI (US); Brett Allen Pawlanta, Grand Rapids, MI (US); Thomas M. Richardson, Ada, MI (US); Brian Dale Teunis, Fennville, MI (US)

(73) Assignee: X-Rite, Inc., Grand Rapids, MI (US)

( * ) Notice: Subject to any disclaimer, the term of this patent is extended or adjusted under 35 U.S.C. 154(b) by 1345 days.

This patent is subject to a terminal disclaimer.

(21) Appl. No.: 11/410,451

(22) Filed: Apr. 25, 2006

(65) Prior Publication Data
US 2006/0245632 A1 Nov. 2, 2006

Related U.S. Application Data

(60) Provisional application No. 60/674,602, filed on Apr. 25, 2005.

(51) Int. Cl.
*G01N 21/55* (2006.01)
*G01J 3/46* (2006.01)
(52) U.S. Cl. .................... 356/445; 356/402; 356/448
(58) Field of Classification Search .................. None
See application file for complete search history.

(56) References Cited

U.S. PATENT DOCUMENTS

| 4,479,718 | A | | 10/1984 | Alman |
| 4,711,580 | A | | 12/1987 | Venable |
| 4,887,906 | A | | 12/1989 | Koehler |
| 5,137,364 | A | * | 8/1992 | McCarthy ............... 356/402 |
| 5,231,472 | A | | 7/1993 | Marcus et al. |
| 5,241,369 | A | | 8/1993 | McNeil et al. |
| 5,313,542 | A | | 5/1994 | Castonguay |

(Continued)

FOREIGN PATENT DOCUMENTS

DE 101 43 602 A1 4/2003

(Continued)

OTHER PUBLICATIONS

International Search Report, PCT/US2006/015600, Sep. 14, 2006, X-Rite, Inc.

(Continued)

*Primary Examiner* — Tarifur Chowdhury
*Assistant Examiner* — Gordon J Stock, Jr.
(74) *Attorney, Agent, or Firm* — McCarter & English, LLP

(57) ABSTRACT

An apparatus for measuring a spatially under-sampled Bidirectional Reflectance Distribution Function (BRDF) of a surface. The apparatus may comprise a first light source directed to illuminate the surface from a first illumination direction, and a plurality of sensors positioned to receive light reflected by the surface. The plurality of sensors may comprise first, second and third sensors positioned to receive light reflected by the surface in first, second and third non-coplanar directions. In various embodiments, the apparatus may also comprise a computer in communication with the plurality of sensors. The computer is configured to convert light sensed by the plurality of sensors into a first appearance property of the surface considering the first, second, and third reflectance directions.

76 Claims, 16 Drawing Sheets

U.S. PATENT DOCUMENTS

| | | | |
|---|---|---|---|
| 5,583,642 | A | 12/1996 | Nakazono |
| 5,640,246 | A | 6/1997 | Castonguay et al. |
| 5,740,079 | A | 4/1998 | Shigemori et al. |
| 6,018,396 | A | 1/2000 | Rapaport et al. |
| 6,362,885 | B1 | 3/2002 | Osumi et al. |
| 6,373,573 | B1 * | 4/2002 | Jung et al. ............. 356/419 |
| 6,539,325 | B1 | 3/2003 | Numata et al. |
| 6,557,397 | B2 | 5/2003 | Langsch |
| 6,577,397 | B1 | 6/2003 | Wadman |
| 6,707,553 | B1 * | 3/2004 | Imura ............. 356/402 |
| 6,772,151 | B1 | 8/2004 | Johnston et al. |
| 7,046,375 | B2 * | 5/2006 | Bischoff et al. ............. 356/600 |
| 7,064,830 | B2 | 6/2006 | Giorgianni et al. |
| 7,130,033 | B2 | 10/2006 | Delacour |
| 7,154,505 | B2 | 12/2006 | Coulthard |
| 7,259,852 | B2 | 8/2007 | Masuda |
| 7,277,174 | B2 | 10/2007 | Yamanouchi et al. |
| 7,466,415 | B2 * | 12/2008 | Gibson et al. ............. 356/402 |
| 2001/0036309 | A1 | 11/2001 | Hirayama et al. |
| 2002/0097400 | A1 | 7/2002 | Jung et al. |
| 2002/0163640 | A1 | 11/2002 | Masuda |
| 2002/0167669 | A1 * | 11/2002 | Schwarz ............. 356/446 |
| 2004/0051874 | A1 | 3/2004 | Kubitzek |
| 2004/0218182 | A1 | 11/2004 | Alman et al. |
| 2004/0239919 | A1 | 12/2004 | Schwarz |
| 2005/0018195 | A1 | 1/2005 | Lex |
| 2006/0023202 | A1 | 2/2006 | Delacour |
| 2006/0227137 | A1 * | 10/2006 | Weyrich et al. ............. 345/426 |
| 2008/0291449 | A1 | 11/2008 | Rodrigues et al. |

FOREIGN PATENT DOCUMENTS

| | | |
|---|---|---|
| EP | 1 217 346 | 6/2002 |
| FR | 2 860 869 A1 | 10/2003 |
| WO | WO 2005/072448 A2 | 8/2005 |
| WO | WO 2008/063606 A2 | 5/2008 |
| WO | WO 2008/121358 A1 | 10/2008 |

OTHER PUBLICATIONS

Ershov, et al., Rendering Pearlescent Appearance Based on Paint-Composition Modelling, Eurographics, 2001, vol. 20 No. 3.

Harvey, Light Scattering Properties of Optical Surfaces, Dissertation, University of Arizona, 1976.

Standard Practice of Angle Resolved Optical Scatter Measurements on Specular or Diffuse Surfaces, ASTM International; Designation: E 2387-05.

Baxter, et al., *A viscous paint model for Interactive Applications*, University of North Carlolina at Chapel Hill, 2004, available at http://gamma.cs.unc.edu/VISCOUS/.

Baxter, et al., *A viscous paint model for Interactive Applications*, Computer Animation and Virtual Worlds Journal, Jul. 2004.

William V. Baxter, Jeremy Wendt, and Ming C. Lin, "IMPaSTo: A realistic, interactive model for paint." In Stephen N. Spencer (ed.), *Proceedings of the 3rd International Symposium on Non-Photorealistic Animation and Rendering*, Annecy, France, Jun. 5-7, 2004.

Caivano, Jose Luis, *Cesia: A system of Visual Signs Complementing Color*, Color research and application 16(4), Aug. 1991.

Caivano, Jose Luis, *The Representation of the Visual World in Photography*, Society for Imaging Science and Technology, 2008, p. 189-193.

Ershov, et al., *Reverse Engineering approach to appearance-based design of metallic and pearlescent paints*, The Visual Computer, Oct. 12, 2004.

William Baxter and Ming Lin, *A Versatile Interactive 3D Brush Model*, Proc. of Pacific Graphics, Oct. 2004, available at http://gamma.cs.unc.edu/BRUSH/.

William V. Baxter, Vincent Scheib, Ming C. Lin, and Dinesh Manocha "DAB: Interactive Haptic Painting with 3D Virtual Brushes." in Eugene Fiume (ed.), *Proceedings of the 28th Annual Conference on Computer Graphics and Interactive Techniques, SIGGRAPH 2001*, Los Angeles, CA, Aug. 12-17, 2001, pp. 461-468. Available at http://gamma.cs.unc.edu/DAB/.

Curtis, et al., "Computer Generated Watercolor." In *SIGGRAPH 2001*, Los Angeles, CA, Aug. 3-8, 1997, pp. 461-468. Available at http://grail.cs.washington.edu/projects/watercolor/.

Nelson S.-H. Chu and C.-L. Tai, Real-time Painting with an Expressive Virtual Chinese Brush. *IEEE Computer Graphics and Applications*, Sep./Oct. 2004 (vol. 24, No. 5). pp. 76-85.

Nelson S.-H. Chu and C.-L. Tai, An Efficient Brush Model for Physically-Based 3D Painting, *Proc. of Pacific Graphics 2002*, Oct. 9-11, Beijing, China, *IEEE Press*.

Jeng-Sheng Yeh, Ting-Yu Lien, Ming Ouhyoung, "On the Effects of Haptic Display in Brush and Ink Simulation for Chinese Painting and Calligraphy", Proc. of Pacific Graphics 2002 (PG2002), pp. 439-441, Oct. 2002, Beijing, China, IEEE Press.

http://www.refractometer.com/abberefrac.html (last visited on Mar. 26, 2010)—Link not working.

http://www.microphotonics.com/se500.html (as of Mar. 13, 2006 using wayback machine).

http://www.datacolor.com/uploads/broch_multifx10_en.pdf (as of Mar. 13, 2006 using wayback machine).

BBC News, *Laser spots paper 'fingerprints'*, available at http://news.bbc.co.uk/2/hi/technology/4741809.stm, Aug. 3, 2005.

X-Rite, The Color Guide and Glossary, Communication, measurement, and control for Digital Imaging and Graphic Arts, 2004.

* cited by examiner

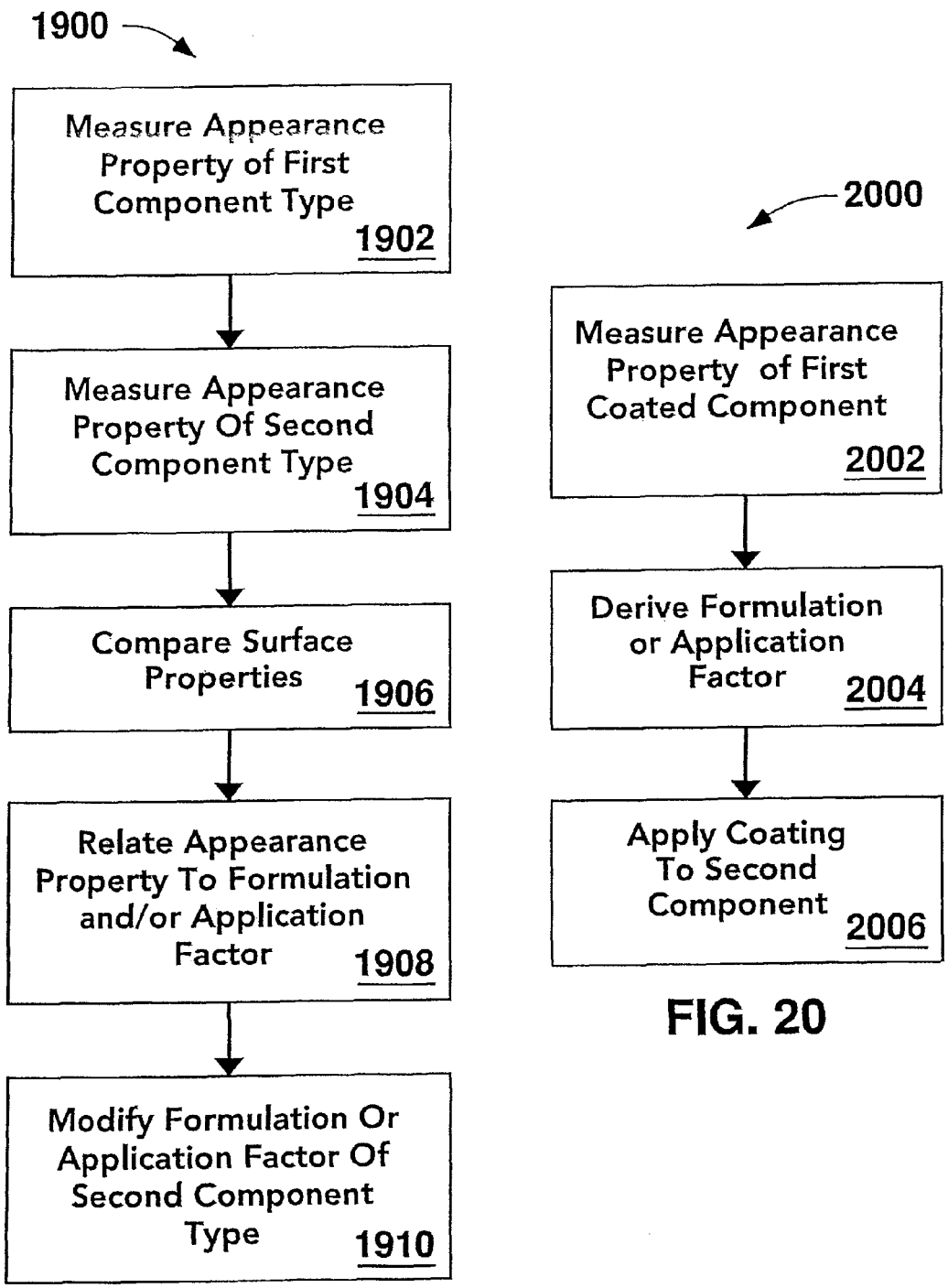

MEASURING AN APPEARANCE PROPERTY OF A SURFACE USING A SPATIALLY UNDER-SAMPLED BIDIRECTIONAL REFLECTANCE DISTRIBUTION FUNCTION

CROSS-REFERENCE TO RELATED APPLICATION

This application claims the benefit of U.S. Provisional Application No. 60/674,602 filed on Apr. 25, 2005, which is incorporated herein by reference.

BACKGROUND

Many methods and devices have been developed for measuring and describing the visual appearance of objects. These methods and devices are useful in a variety of contexts. For example, measurements of the visual appearance of an object can reveal properties of any paints, pigments, specialty coatings, surface treatments, etc., that may be present on the object. Also, for example, measurements of the visual appearance of an object can be used to create computer models, set production tolerances, etc. It is known to use various devices to provide spectral measurements of a surface of an object. Existing devices, however, either produce results of limited detail or are exorbitant in cost, size, and the time necessary for measurements.

For example, it is known to use discrete multi-angle spectrometers that measure reflectance over a limited number of viewing and illumination directions. An example of such a device is the MA68 available from X-RITE. All of these devices, however, either consider a limited number of viewing directions (e.g., coplanar directions), or consider data derived from all viewing angles together, for example, by summing or averaging over all directions. As a result, known discrete multi-angle spectrometers provide results that do not reflect directional variations in surface appearance. Referring to the coatings industry, these results can be useful to measure some properties of surfaces including conventional paints, pigments, and coatings. They are not as useful, however, for measuring properties of surfaces having specialized paints, pigments, and other specialty coatings that have different appearances when viewed from different angles, such as those that appear today on cars, boats, currency, consumer plastics, cosmetics, etc. For example, limited sample multi-angle spectrometers are not as useful for measuring properties of interference coatings such as, for example, pearlescent automotive paints that appear one color (e.g., white) from one angle and a second color (e.g., pink) from another angle. They also typically do not provide detailed enough results to tie properties of a surface back to physical features of the surface, for example, due to coating formulation and/or application process factors.

Some of the shortcomings of known discrete multi-angle spectrometers are addressed by devices that measure the complete Bidirectional Reflectance Distribution Function (BRDF) of a surface, such as goniospectrophotometers and parousiameters. The complete BRDF generated by these devices provides a rich characterization of the scatter off of a surface as a function of illumination angle, viewing angle, wavelength and other variables. Both of the known devices for measuring BRDF, however, have significant drawbacks.

Goniospectrophotometers, such as the GCMS-4 Gonio-Spectro-Photometric Colorimeter available from MURAKAMI, measure the complete BRDF by scanning both illumination and detection angles, typically over a complete hemisphere. Although they can provide good results, the devices are extremely large and expensive. Also, it can take several hours to scan illumination and detection angles over a complete hemisphere, making real-time applications impossible. Parousiameters, such as the one described in U.S. Pat. No. 6,557,397 to Wademan, measure the complete BRDF by projecting a range of illumination and detection angles onto a hemispheric screen and imaging the screen using a camera. The error of these devices, however, is directly related to the size of the hemispherical screen, and the devices cannot acceptably measure samples with an area greater than 10% of their screen's area. As a result, parousiameters are often large and bulky. Also, slots in the screen, and the limited dynamic range of most high resolution cameras further limit the device. In addition, because both goniospectrophotometers and parouiameters measure illumination and viewing angles over a complete hemisphere, noise issues can become a significant factor.

SUMMARY

In one general aspect, the invention is directed to an apparatus for measuring a spatially under-sampled Bidirectional Reflectance Distribution Function (BRDF) of a surface. The apparatus may comprise a first light source directed to illuminate the surface from a first illumination direction, and a plurality of sensors positioned to receive light reflected by the surface. The plurality of sensors may comprise first, second and third sensors positioned to receive light reflected by the surface in first, second and third non-coplanar directions. In various embodiments, the apparatus may also comprise a computer in communication with the plurality of sensors. The computer is configured to convert light sensed by the plurality of sensors into a first appearance property of the surface considering the first, second, and third reflectance directions.

In another general aspect, the invention is directed to methods for measuring a spatially under-sampled Bidirectional Reflectance Distribution Function (BRDF) of a surface. The methods comprise the steps of illuminating the surface with a first light source incident on the surface from a first illumination direction, and sensing light of a plurality of wavelengths reflected by the surface in a plurality of reflectance directions. The plurality of reflectance directions include a first reflectance direction, a second reflectance direction and a third reflectance direction. The methods also comprise the step of converting the light into a first appearance property of the surface considering the first, second, and third reflectance directions.

Various other embodiments of the invention are directed to systems for measuring a spatially under-sampled Bidirectional Reflectance Distribution Function (BRDF) as well as practical applications. In various aspects, the invention is directed to methods of matching the appearance of coatings applied to two components, methods of repairing a device, and methods of finding the identity of an unknown object.

BRIEF DESCRIPTION OF THE FIGURES

Embodiments of the present invention are described herein, by way of example, in conjunction with the following figures, wherein:

FIGS. 17-22 show flow charts illustrating process flows according to various embodiments of the present invention.

DETAILED DESCRIPTION OF THE INVENTION

Embodiments of the present invention are directed to methods and apparatuses for measuring and/or analyzing a spatially under-sampled Bidirectional Reflectance Distribution Function (BRDF) of a surface. When light is incident on a surface, a portion of the light is reflected, scattered or otherwise directed away from the surface over various directions. The BRDF of a surface is an expression of the intensity of this reflectance over all wavelengths and reflectance directions as a function of illumination angle and other variables (e.g., polarization). According to various embodiments, the BRDF of a surface is spatially under-sampled by measuring the intensity of reflectance at only a discrete number of reflectance directions. In various embodiments, the discrete reflectance directions may be non-coplanar. The measured reflectance may then be processed to derive appearance properties of the surface under observation. The appearance properties may reflect directional variation in the appearance of the surface, as captured by the measured reflectance.

Figure 1:
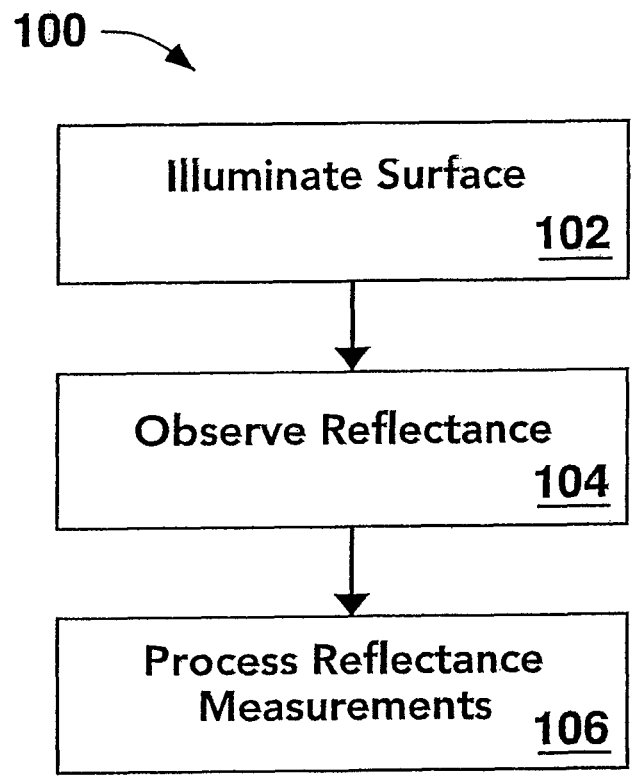
FIG. 1 shows a flow chart illustrating a process flow according to various embodiments of the present invention.

FIG. 1 shows a flow chart illustrating a process flow 100 for measuring and processing a spatially under-sampled BRDF of a surface according to various embodiments. At step 102, light may be directed toward the surface. The light may be formed into one or more beams, which may be collimated or non-collimated. The light may originate from one or more broad spectrum illumination sources and may be incident on the surface from one or more illumination directions. The number of illumination sources and illumination directions may vary based on the particular application. It will be appreciated, however, that increasing the number of illumination sources and/or directions may increase the quality of the resulting BRDF. It will be appreciated that, the illumination direction or directions may form any angle with the surface normal. In various embodiments, however, the illumination direction or directions may form angles with the surface normal of between zero and sixty-five degrees (e.g. zero degrees, 45 degrees, etc.).

At step 104, the intensity of the reflectance off of the surface in a plurality of discrete reflectance directions may be measured. It will be appreciated that these measured reflectances, along with the corresponding reflectance directions, represent a spatially under-sampled BRDF of the surface. In various embodiments, the complete set of reflectance directions may be non-coplanar. Also, in various embodiments, multiple measurements may be taken at each reflectance direction, with each measurement recording the reflectance intensity at a particular wavelength or wavelength range. In various embodiments, the measurements may be taken from fixed sensors, with one sensor fixed on each of the plurality discrete reflectance directions. It will be appreciated that because the reflectance is being measured only in discrete directions, and not in every direction, that the time necessary to measure the reflectance may be less than that taken by complete BRDF devices (e.g., goniospectrophotometers and parousiameters). In various embodiments, the measurements may be taken in under five seconds.

The spatially under-sampled BRDF may be expressed as a series of reflectance vectors representing the observed intensities at each reflectance direction. For example, each observed reflectance direction may have a vector pointing in the reflectance direction with a magnitude equal to the observed reflectance intensity in the reflectance direction. It will be appreciated that if multiple wavelengths or wavelength ranges are observed in a reflectance direction, then reflectance directions may have a vector corresponding to each of the wavelengths or wavelength ranges.

Figure 2:
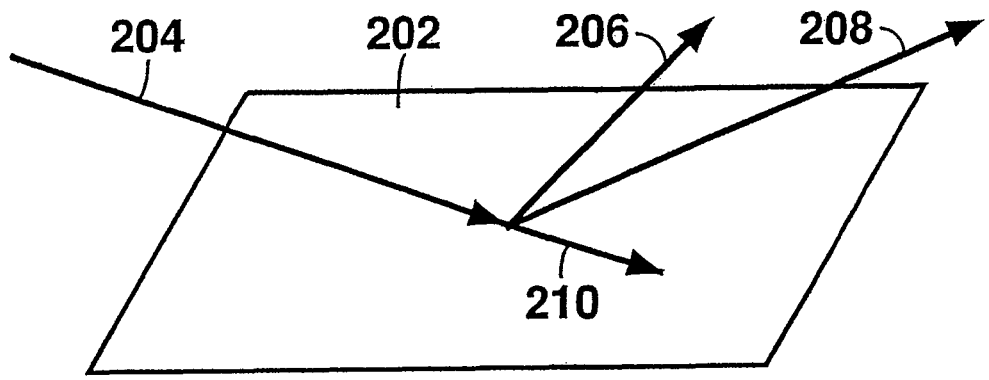
FIG. 2 shows a diagram of reflectance from a surface according to various embodiments of the present invention.
Figure 3:
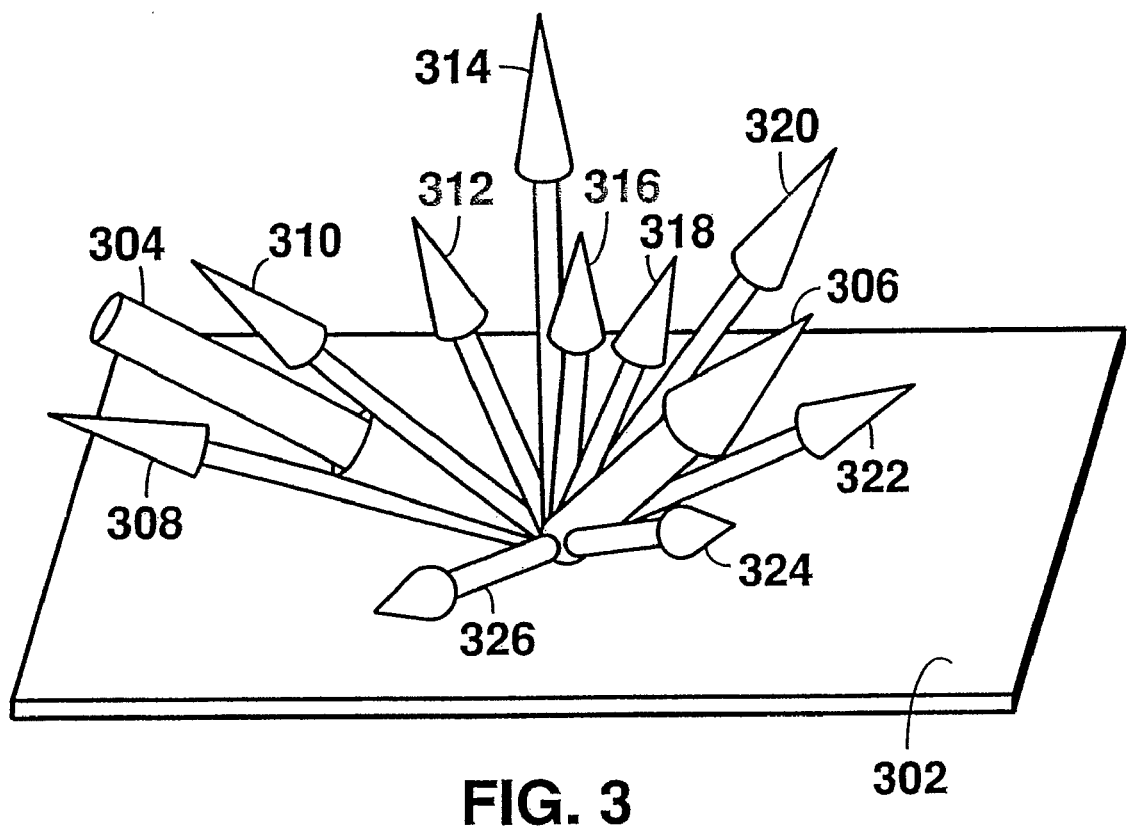
FIG. 3 shows a diagram of reflectance from a surface according to various embodiments of the present invention.

As an illustration, FIG. 2 shows an exemplary surface 202 with light incident on the surface 202 from an illumination direction 204. Three discrete non-coplanar reflectance directions 206, 208, 210 are observed. FIG. 3 shows another exemplary surface 302 according to various embodiments having incident light from one illumination direction 304 and eleven observed reflectance directions 306, 308, 310, 312, 314, 316, 318, 320, 322, 324 and 326. It will be appreciated that the number and identity of the reflectance directions may vary. For example, in various embodiments, there may be between five and fifteen reflectance directions. Also, in various embodiments, the reflectance directions may include industry standard reflectance directions (e.g., those having aspecular angles of 15, 25, 45, 75 and 100 degrees.) Also, in various embodiments, at lease one of the reflectance directions may be chosen orthogonal to the illumination direction relative to a surface normal of the surface.

Figure 4:
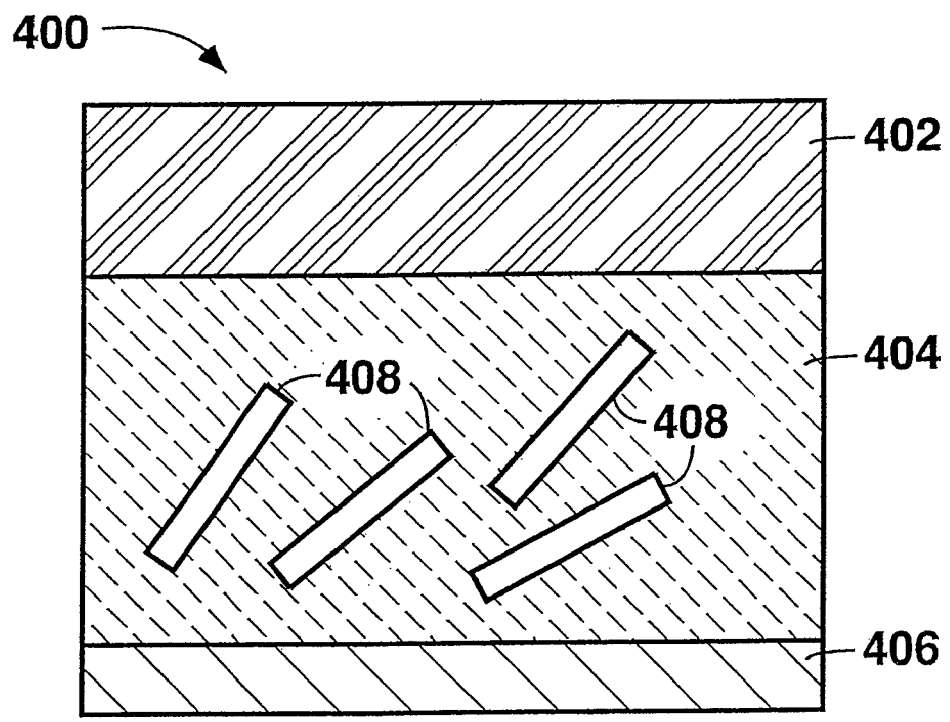
FIG. 4 shows a diagram of a surface coating according to various embodiments of the present invention.

In various embodiments, the number of observed reflectance directions may be chosen based on a desired resolution of results and/or the complexity of the surface to be measured. For example, each layer and/or materials contained in the layers of a surface may have a number of physical properties (e.g., roughness, local slope, curvature, real and imaginary portions of the index of refraction, etc.). In various embodiments, it may only be necessary to measure a minimum number of reflectance directions to obtain enough independent relationships to solve for all desired variables. For example, a minimum number of observed reflectance directions may be chosen according to the following:

$$\text{Minimum Number of Reflectance Directions} = 2L + M \qquad (1)$$

where L is the number of physical layers of the surface through which light can potentially scatter, and M is the number of different materials contained in the layers (e.g., pigments, metallic flakes, etc.). For example, FIG. 4 shows an exemplary surface 400 that may be observed according to various embodiments. The surface 400 has a specialty coating, such as, for example, an interference or pearlescent coating, discussed above. The surface 400 includes three layers, clear coat 402, pigment layer 404 and substrate 406, as well as one material contained in the layers (e.g., metal flakes 408).

Accordingly, a minimum number of observed reflectance directions for the surface 400 would be seven. It will be appreciated that useful readings may be obtained using less than the minimum number of reflectance directions according to Equation 1, however, in that case, the observed reflectance may not capture the contribution to BRDF from each of the surface features.

As the number of observed discrete reflectance directions is increased, the quality of the results obtained may also increase. For example, in various embodiments, additional physical properties may be measured. It will be appreciated however, that increasing the number of observed discrete reflectance directions will also increase the complexity, time necessary to observe at all reflectance directions, and noise. Accordingly, in various embodiments, it may not be necessary to observe more reflectance directions than the following:

$$\text{Maximum Number of Reflectance Directions}=6L+6M \quad (2)$$

where L and M are defined as above. Equation 2 may define the number of reflectance directions necessary to have an independent relationship for each physical property to be measured.

Figure 5:
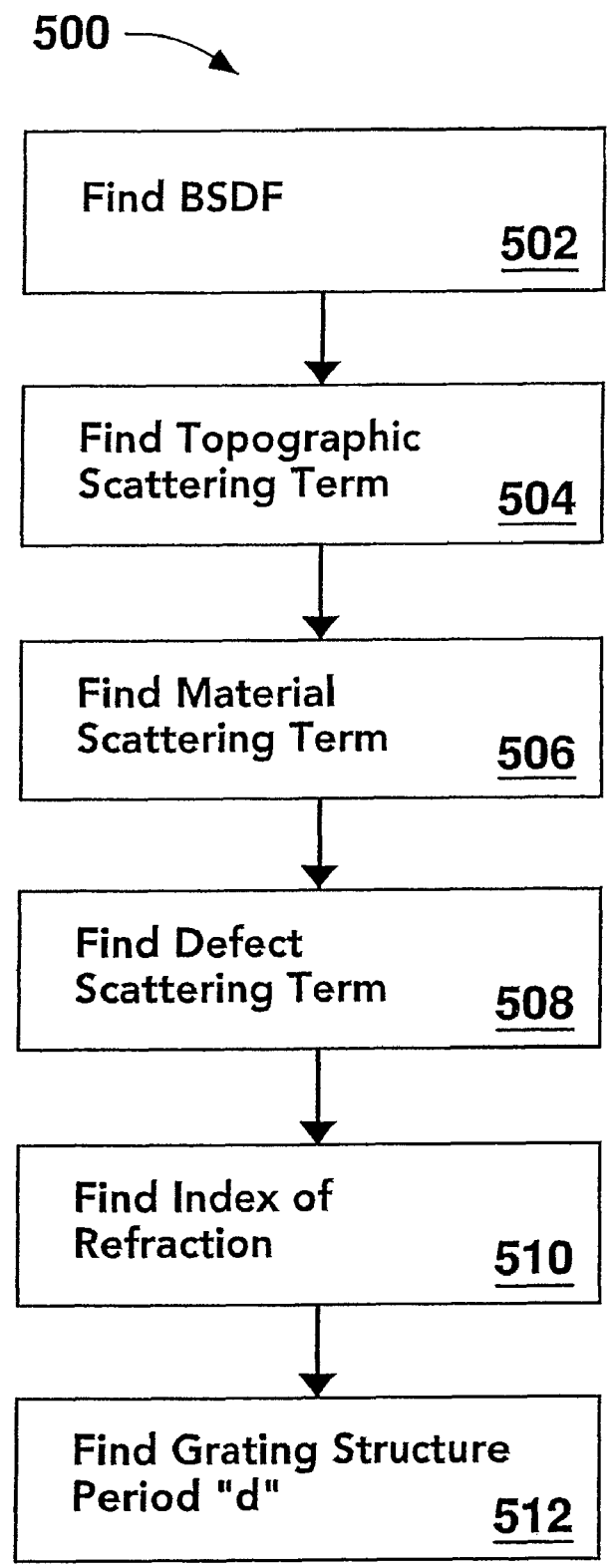
FIG. 5 shows a flow chart illustrating a process flow according to various embodiments of the present invention.
Figure 8:
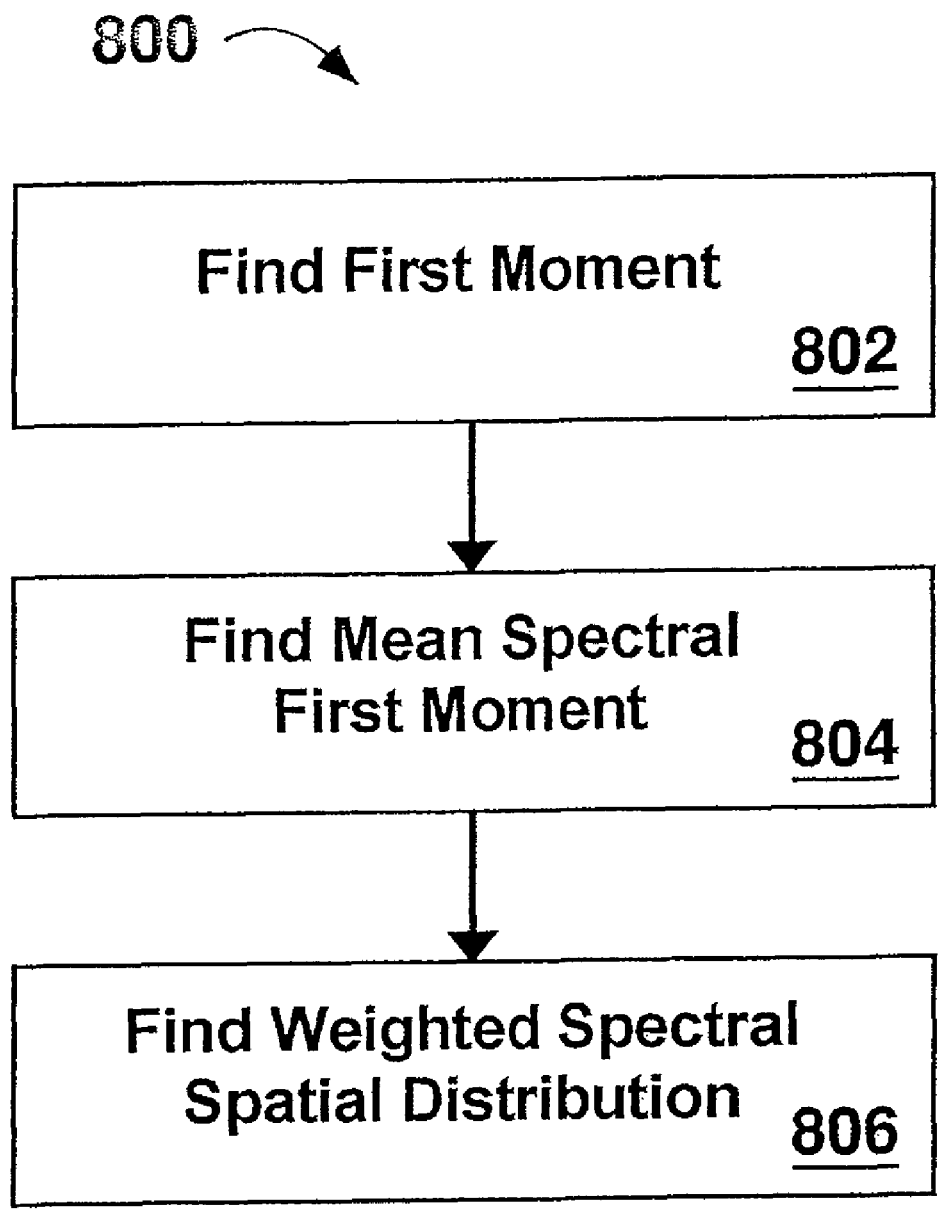
FIG. 8 shows a flow chart illustrating a process flow according to various embodiments of the present invention.

Referring back to FIG. 1, at step 106, the reflectance measured at step 104 may be processed to generate an appearance property or properties of the surface. The spatially undersampled BRDF itself may be considered an appearance property of the surface, though it will be appreciated that other appearance properties may be generated, for example, by manipulating the BRDF. At least one of the appearance properties may reflect directional differences in the appearance of the surface that are inherent in the measured reflectance intensities and directions. In various embodiments, additional appearance properties may be found by performing manipulations to the BRDF. For example, FIG. 5 shows a process flow 500, described below, for processing measured reflectance by plugging the measured reflectance into a mathematical model for the BRDF of the surface and performing certain mathematical manipulations. As another example, FIG. 8 shows a process flow 800 for analyzing various moments of the BRDF data.

The appearance properties generated at step 106 may yield information about the composition and features of the surface under measurement (e.g., physical properties). For example, in the coatings industry, properties of the formulation and application process of any coatings present on the surface may be found. For some physical properties, closed form solutions may exist that allow values for the properties to be derived directly from the measured reflectance or BRDF. For example, as discussed below, a grating structure period may be derived from the BRDF, and may relate directly to the distance between regularly spaced features of the surface. Also, some physical properties may be derived using experimental methods. For example, appearance properties of surfaces with known physical properties may be measured. A database may then be created showing correlations between appearance properties and physical properties. When a surface with unknown physical properties is measured, appearance properties (e.g., BRDF, and/or values derived therefrom) may be compared to the database to find the unknown physical properties.

FIG. 5 shows the process flow 500 for processing measured reflectance (e.g. BRDF) and deriving additional appearance properties of the surface using mathematical models based on the BRDF. Referring to FIG. 5, at step 502, the BRDF may be converted to a Bidirectional Scatter Distribution Function (BSDF). The BSDF represents the portion of the BRDF due to scattering of incident light. To calculate the BSDF, the specular component of BRDF is subtracted from the BRDF. The specular component is that portion of the BRDF that is due to Fresnel reflection of incident light. The specular component is concentrated in a reflectance direction that is related to the illumination direction such that the angle of incidence of the illumination direction is equal to the angle of reflectance of the specular reflectance direction. For example, referring to FIG. 3, the illumination direction 304 forty-five degrees from the surface and 45 degrees from the surface normal. According, the specular component is directed in reflectance direction 306, which is also 45 degrees from the surface and surface normal. It will be appreciated that if there is more than one illumination direction, then the specular component may be concentrated in more than one angle.

The specular component may be subtracted from the BRDF in a number of different ways. For example, one of the observed reflectance directions may be the specular direction. In this case, the BSDF may be found by subtracting the contribution of this reflectance direction from the overall BRDF. In embodiments where the specular direction is not one of the observed reflectance directions, then the specular component may be approximated based on the responses at observed reflectance directions near the specular direction. The approximation of the specular component may then be subtracted from the BRDF.

Referring again to FIG. 5, a topographic scattering term of the BSDF may be found at step 504. It will be appreciated that the BSDF may be expressed as:

$$BSDF=(16\pi^2/\lambda^4)\cos^2\theta_i \Phi_{ba}(\phi_s)R_a(\theta_i)S_z(f) \quad (3)$$

where $S_z(f)$ is the two dimensional Power Spectral Distribution (PSD) of any height fluctuations (Z) of the surface. Accordingly, dividing the BSDF by $(16\pi^2/\lambda^4)\cos^2\theta_i$ yields a topographic scattering term that is proportional to height fluctuations on the surface.

At step 506 a material scattering term may be found. The material scattering term may be indicative of fluctuations in the composition or density of the surface material (e.g., homogeneity, bubbles, inclusions, randomly dispersed or distributed pigments smaller than approximately 30 microns, etc.). It will be appreciated that the BSDF may be expressed as:

$$BSDF=(1/\lambda^2)\Phi_{ba}(\phi_s)R_a(\theta_i)S_m(f)$$

where $S_m(f)$ is the PSD of the perturbation of the material response for scattering. This PSD may be related to specific models of the material inhomogeneities, such as the magnitudes and spatial distribution of variations in composition. A material scattering term may then be found by dividing the BSDF by $(1/\lambda^2)$. Experimental methods may be used to tie values of the material scattering term (e.g., an appearance property) to particular types, sizes, etc. of fluctuations in composition and/or density of the surface (e.g., physical properties).

At step 508, a defect scatting term of the BSDF may be found. Defect scattering occurs when a surface feature or bulk property perturbation is localized and/or isolated spatially (e.g., pits or bumps in the surface, individual inclusions in an otherwise homogeneous bulk material). It will be appreciated that, if the defects are randomly distributed, then the BSDF may be expressed as:

$$BSDF=(1/\lambda^2)\Phi_{ba}(\phi_s)R_a(\theta_i)S_d(f) \quad (5)$$

where $S_d(f)$ is the PSD of the collection of defects in the surface. Accordingly, a defect scattering term may be calculated by dividing the BSDF by $(1/\lambda^2)$. Experimental methods may be used to tie particular values of the defect scattering term to particular defect types and locations. It will be appreciated from comparing Equations 4 and 5, that $S_d(f)$ and $S_m(f)$ may have the same value. Accordingly, Equation 4 may be applied to a surface that is measured or assumed to be relatively free of blemishes. On the other hand, Equation 5 may be applied to surfaces with known defects.

Figure 6:
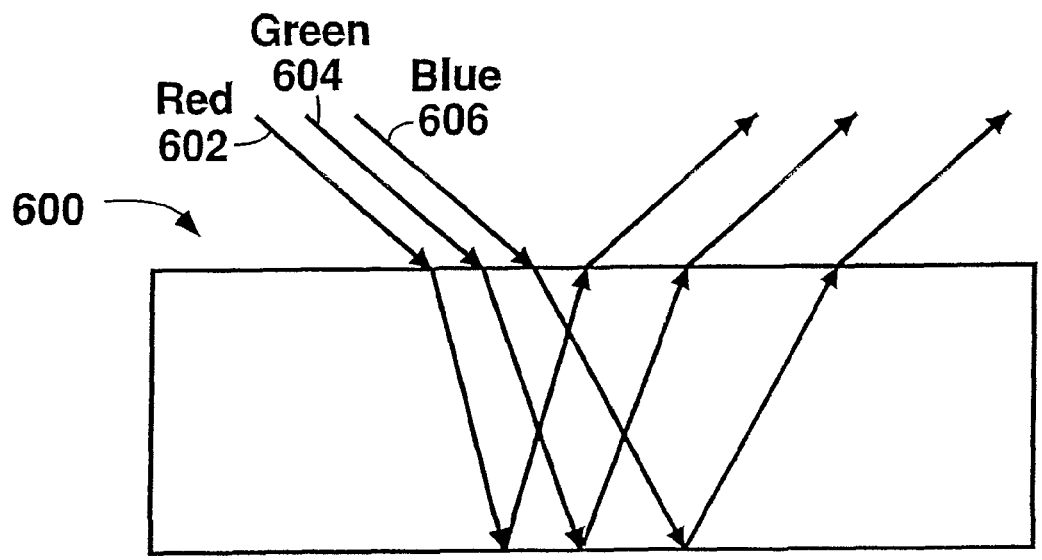
FIG. 6 shows a diagram of refraction by a surface according to various embodiments of the present invention.

At step 510, an index of refraction of the surface may be found. FIG. 6 shows a surface 600 having red 602, green 604, and blue 606 beams incident thereon. FIG. 6 illustrates how refraction may cause the different beams 602, 604, 606 to behave differently. Snell's law may be used to find the index of refraction of the surface as follows:

$$n_1 \sin \theta_1 = n_2 \sin \theta_2 \quad (6)$$

where $n_1$ is the index of refraction of the surface, $n_2$ is the index of refraction of the medium between the surface and the observation points, $\theta_1$ is the angle of the illumination direction and $\theta_2$ is the refraction angle at a given wavelength. The index of refraction may be considered a physical property of the surface, however, it will be appreciated that additional physical properties (e.g., the grating structure period below) may be derived based on the index of refraction.

Figure 7:
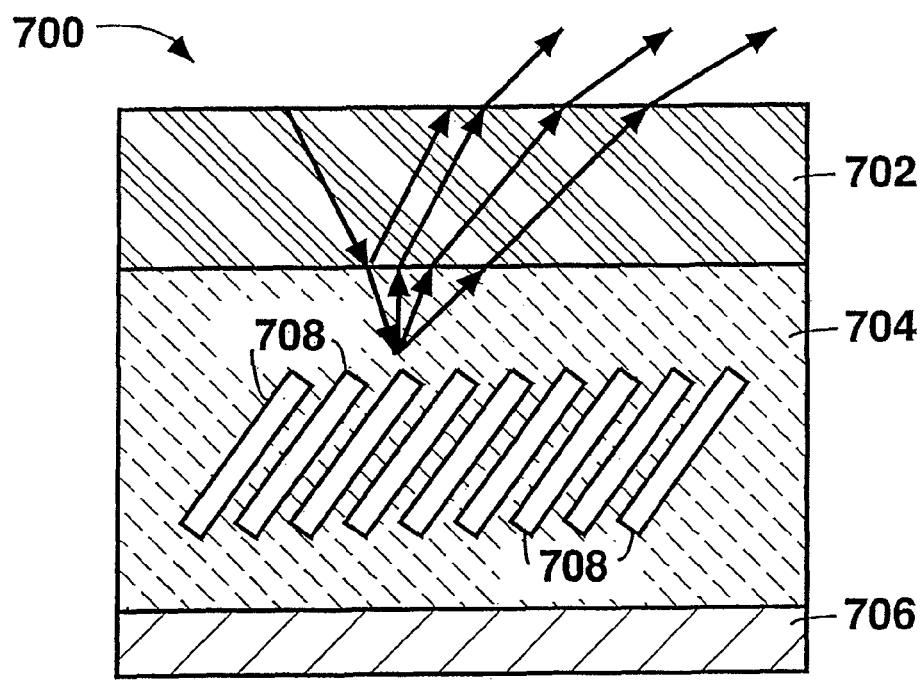
FIG. 7 shows a diagram of diffraction and/or interference by a surface according to various embodiments of the present invention.

At step 512, a grating structure period of the surface may be found. The grating structure period may provide information about surface features, interface features, bulk material structure, pigments, particles, flakes, etc., present in the surface that have an ordered structure. Such ordered features may cause diffraction and/or interference in reflected light based on the grating structure period of the features. For example, FIG. 7 shows an exemplary surface 700 having a series of flakes 708 embedded therein at a regular or semi-regular interval and orientation. Note that the surface 700 may include a plurality of layers 702, 704 and 706. The grating structure period of the surface 700 may reflect the distance between and/or orientation of the flakes 708. The grating structure period may be found as follows:

$$\lambda = 2nd \sin(\theta) \quad (7)$$

where n refractive index of the surface, d is the period of the grating line structure and $\theta$ is the angle at which the wavelength of light is diffracted normal to the grating line structure.

FIG. 8 shows a process flow 800 for deriving values indicative of surface properties using a moment or moments of the BRDF. At step 802 a first moment, or weighted directional response may be found. The weighted direction response may be the vector summation of all of each of the vectors representing the observed intensities and reflectance directions over a given wavelength or wavelength range. It will be appreciated that where multiple wavelengths or wavelength ranges are considered, a weighted directional response may be calculated for each of the considered wavelengths or wavelength responses.

In various embodiments weighting factors may be applied to one or more of the observe reflectance directions. For example, the weighting factors may be chosen so that the resulting weighted BRDF more closely approximates a geometrically uniform distribution of reflectance directions. In various embodiments, weighting factors may be chosen to accentuate reflectance directions that have increased significance for certain surface types. For example, when the surface includes an interference pigment, the reflectance direction having an aspecular angle of −15° may be disproportionately weighed, when the surface includes a retroreflective material, reflectance directions having aspecular angles of 75° and 110° may be disproportionately weighted.

Also, in various embodiments, weighting factors may be chosen to be compatible with various standards. For example, the DIN 6175-2 standard defines color difference formulas with weighting functions that depend on the standard measurement angles, (e.g., the 15/25/45/75/110 angles described above). In various embodiments, the weighting factors may be chosen based on human perceptual studies (e.g., the reflectance directions that humans most strongly perceive may be given higher weighting factors).

It will be appreciated that the weighting factors may also be chosen to more accurately represent the distribution of energy reflected off the surface. For example, if the total energy reflected off the surface is 20 mW, and it is expected that a disproportionately high portion of the 20 mW is expected to be reflected in a certain range of reflectance directions, then intensity measurements taken in that range of reflectance directions may be given a relatively higher weighting compared to other directions. In this way, the spatially under-sampled BRDF may more closely match the actual energy distribution modeled by the full BRDF.

The weighted directional response may be tied to various properties of the surface. For example, in the case of a surface having a coating, the weighted directional response may be used to identify application process variations between two surfaces. For example, when two surfaces differ only in the application process of a coating on the surfaces, the weighted directional response of the first surface can typically be transformed into the weighted directional response of the second surface. The necessary translations, rotations and scaling can be experimentally tied to particular application process variations.

At step 804, a mean spectral first moment of the surface may be found. The mean spectral first moment may be a vector whose direction represents the average spectral first moment. A weighted spectral spatial distribution function may be found at step 806. The weighted spectral spatial distribution may be a function that describes the general line shape defined by the directional endpoints of the weighted directional response. Both of these appearance properties (e.g., the mean spectral first moment and weighted spectral spatial distribution) may be experimentally tied to various physical properties of the surface.

Figure 9:
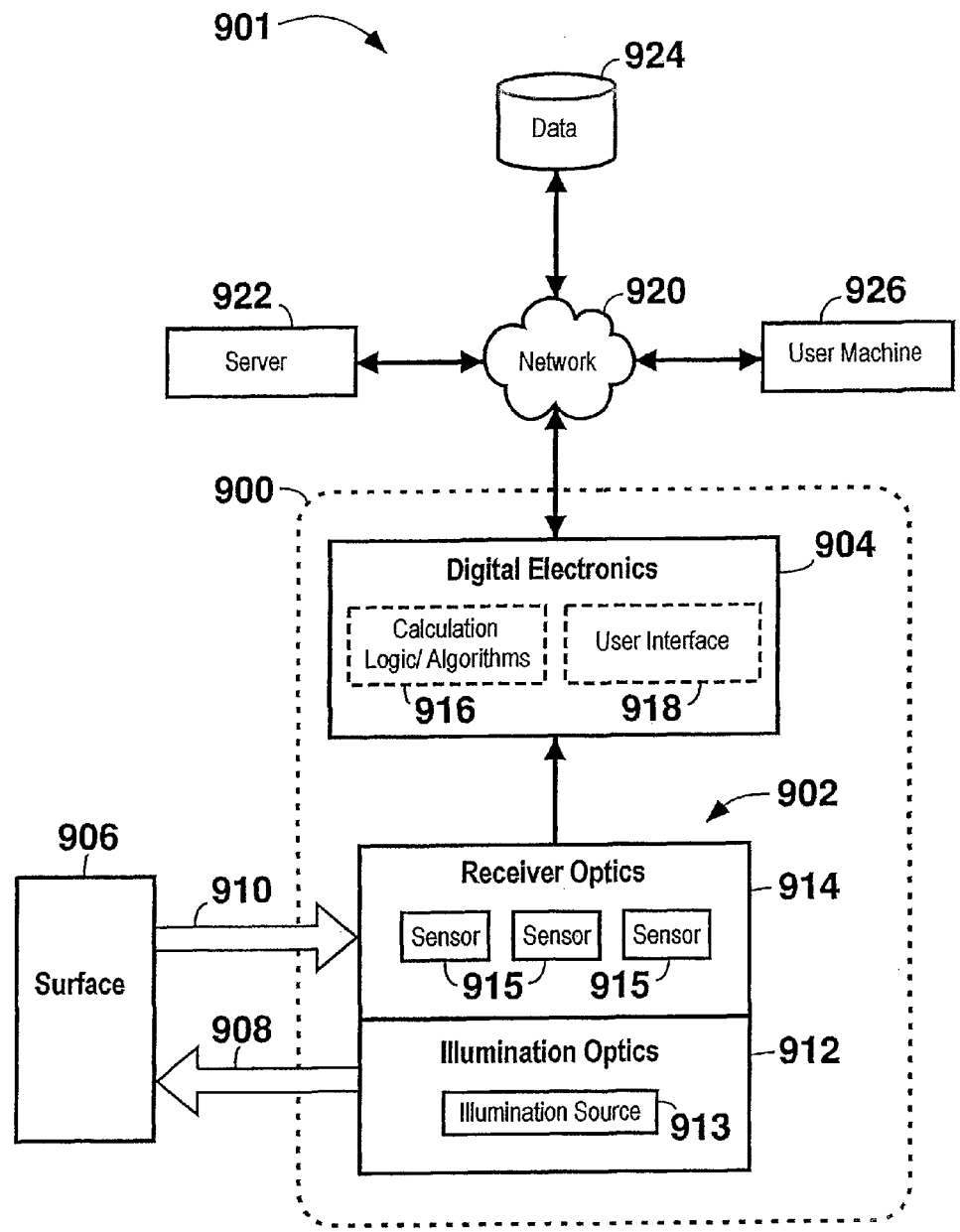
FIG. 9 shows a diagram of a system according to various embodiments of the present invention.

FIG. 9 shows a diagram of a system 901 that may be used to implement methods of measuring and/or analyzing a spatially under-sampled BRDF of a surface, for example, as described above, according to various embodiments. The system 901 includes a measuring device 900, and may also include various other information storage, processing and/or interface devices such as, for example, a server 922, a user machine 926 and/or a database 924. The various devices 900, 922, 924, 926 of the system 901 may be in contact with one another via a network 920, which may be any suitable type of wired or wireless network.

In various embodiments, the measuring device 900 may include an optics unit 902 and an electronics unit 904. The optics unit 902 may include illumination optics 912 configured to direct light 908 towards a surface 906 under inspection, and receiver optics 914 for receiving and sensing the reflectance 910 of the light 908 off of the surface 906. For example, the illumination optics 912 and receiver optics 914 may sense a spatially under-sampled BRDF of the surface 906 as described above. The electronics unit 904 may process the reflectance results generated by the optics unit 902. In various embodiments, the electronics unit 904 may include calculation logic 916 for deriving appearance properties of the surface and/or relating appearance properties to physical properties. A user interface module 918 may present results (e.g., raw reflectance data, appearance properties, physical properties, etc.) to a user of the device 900. In various embodiments, some or all of the processing and presenting of results may be performed by other components of the system for processing (e.g., server 922, database 924, user machine 926). For example, the server 922 and/or user machine 926 may perform processing to derive appearance and/or physical properties; results of the processing may be presented to a user through the user machine 926; and the database 924 may store experimental correlations between measured reflectance and surface properties.

Referring back to the optics unit 902, the illumination optics 912 may include one or more illumination sources 913 configured for directing light 908 toward the surface 906 from one or more illumination directions. The illumination sources 913 may include any kind of suitable illumination source including, for example, an incandescent source, a white LED, etc. In various embodiments, each illumination source 913 may include a plurality (e.g., nine) LED's of various spectral outputs. The LED's may be positioned on a leadless chip carrier or any other kind of installation technology. It will be appreciated that the illumination source or sources 913 may generate light across the wavelengths that are to be measured by the receiver optics 914 as described herein below. In various embodiments, the illumination sources 913 may be configured to generate collimated or non-collimated beams, for example, as described above.

Figure 16:
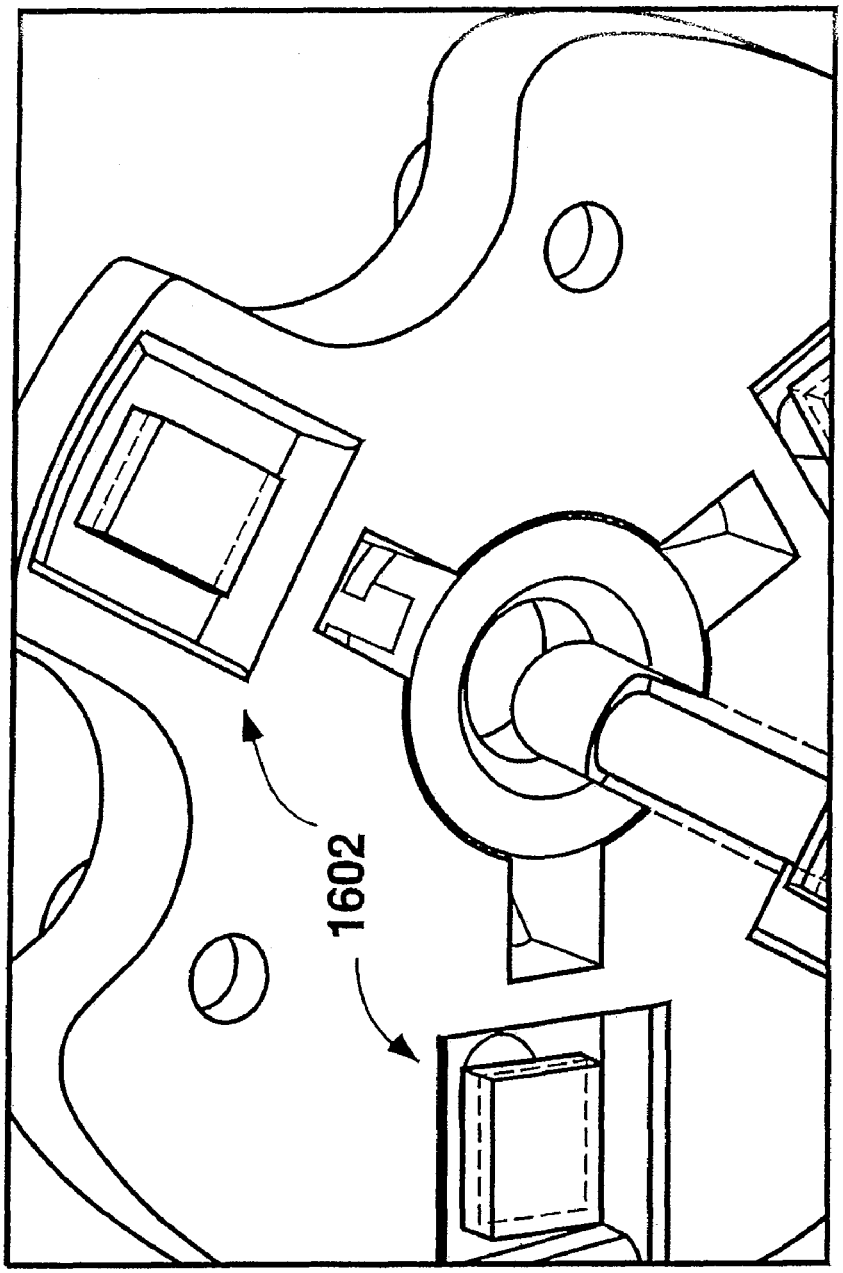
FIG. 16 shows various sensors according to various embodiments of the present invention.

The receiver optics 914 may include one or more sensors 915 positioned along discrete reflectance directions. In various embodiments, the sensors 915 may be positioned to sense non-coplanar reflectance directions such as, for example, reflectance directions 206, 208 and 210 shown in FIG. 2. The sensors 915 may be any kind of imaging or non-imaging sensor or sensor assembly suitable for measuring reflectance (e.g., across multiple discrete wavelength ranges). For example, the sensors 915 may include one or more photodiodes. Any suitable kind of wavelength discriminating equipment (e.g., any kind of band-pass spectral filter, diffraction grating spectrograph, etc.) may be placed in front of the photodiode to sense discrete wavelength ranges. For example, the MAZet Jencolour product line may be used, as shown by sensors 1602 in FIG. 16. In various embodiments, a wheel or other movable device including multiple band-pass filters may be selectively placed in front of the photodiode, allowing one photodiode to measure several discrete wavelength ranges. In other various embodiments, multiple photodiodes may be provided along each reflectance direction, which each of the multiple photodiodes having a separate band-pass filter. It will be appreciated that the sensors 915 may include a wide-band detector capable of discretely measuring multiple wavelength ranges simultaneously such as, for example, a RGB sensor, such as a camera with a logarithmic response or a small array of pixels (e.g., the TCS230 line available from Taos, Inc.).

Figure 10:
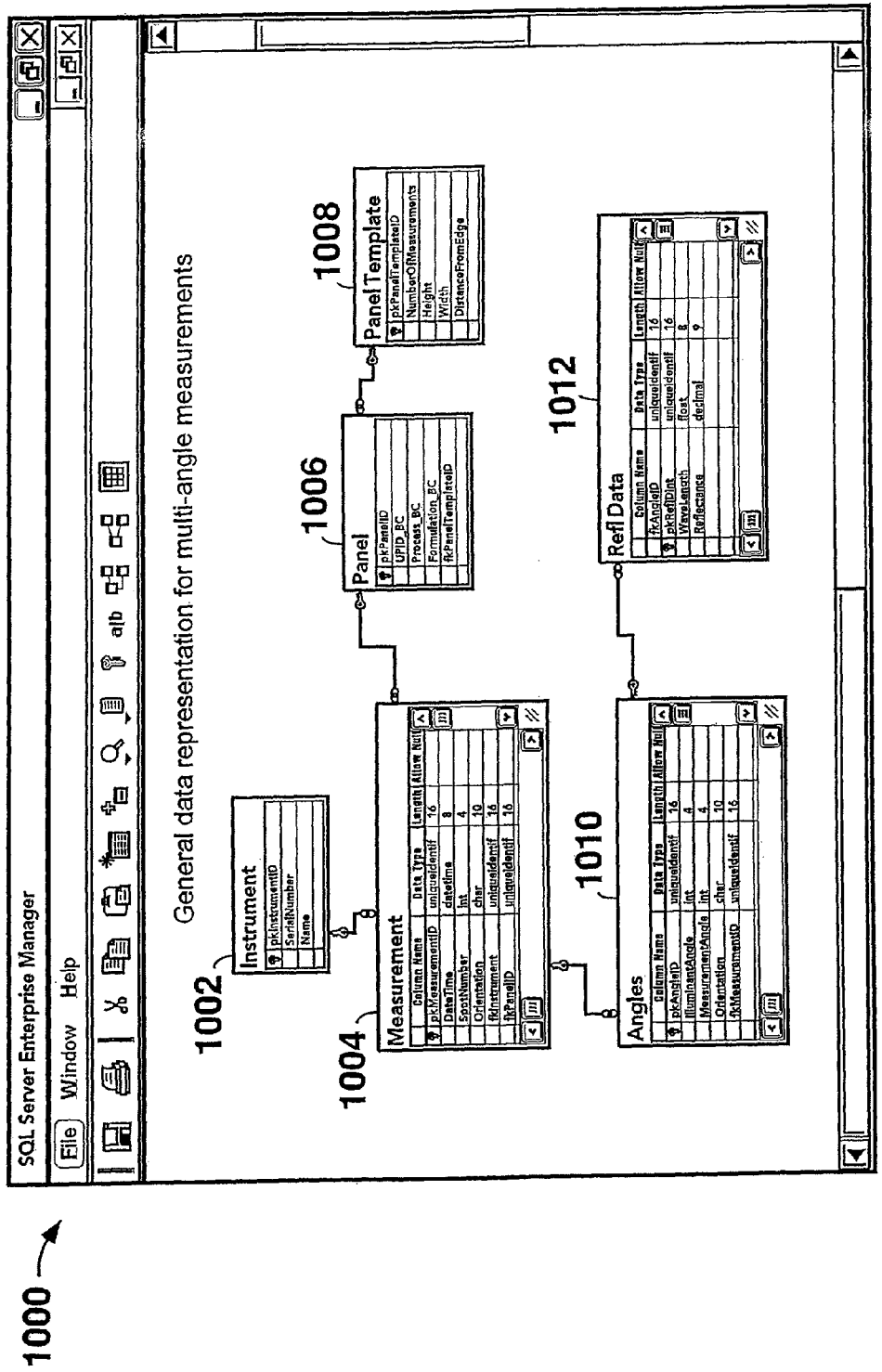
FIG. 10 shows a user interface that may be presented to a user according to various embodiments of the present invention.
Figure 11:
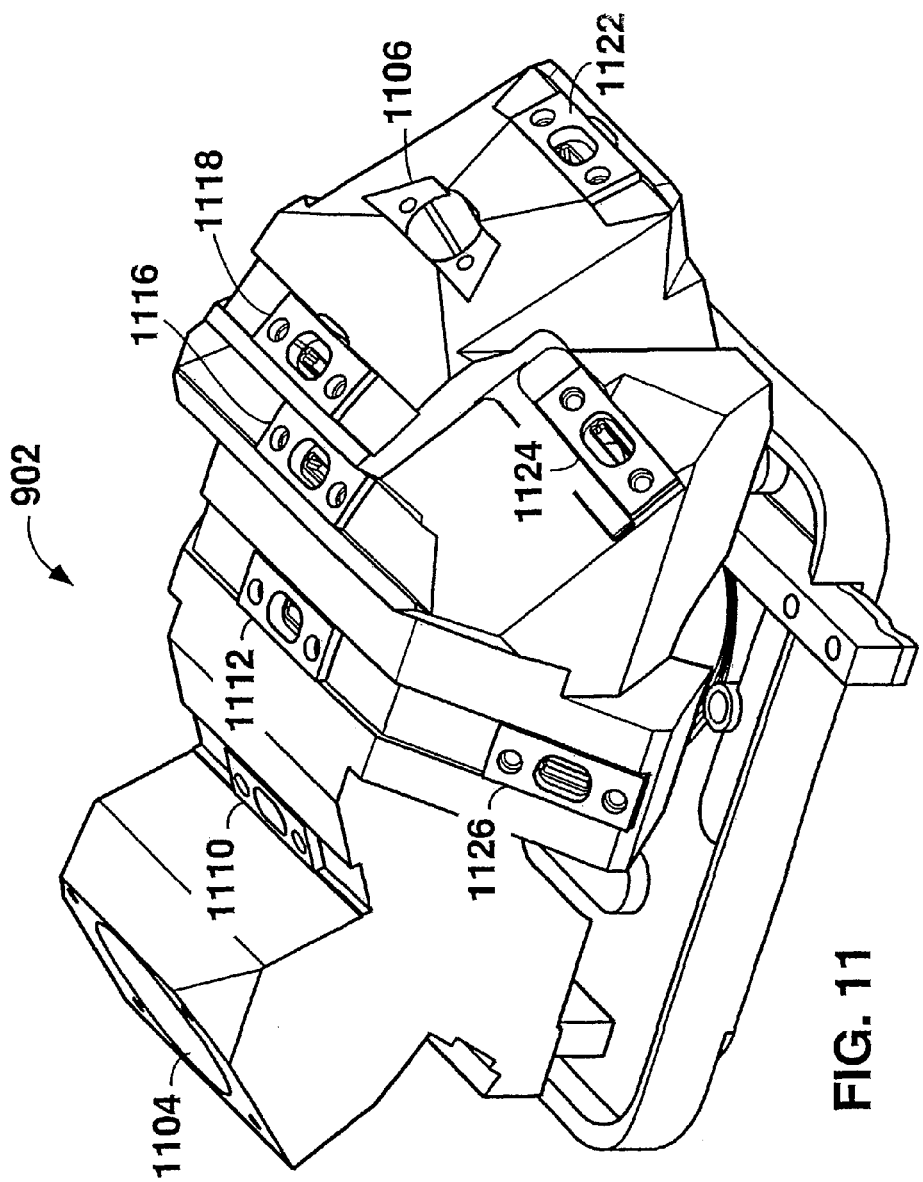
FIGS. 11-14 shows three-dimensional views of an apparatus according to various embodiments of the present invention.
Figure 12:
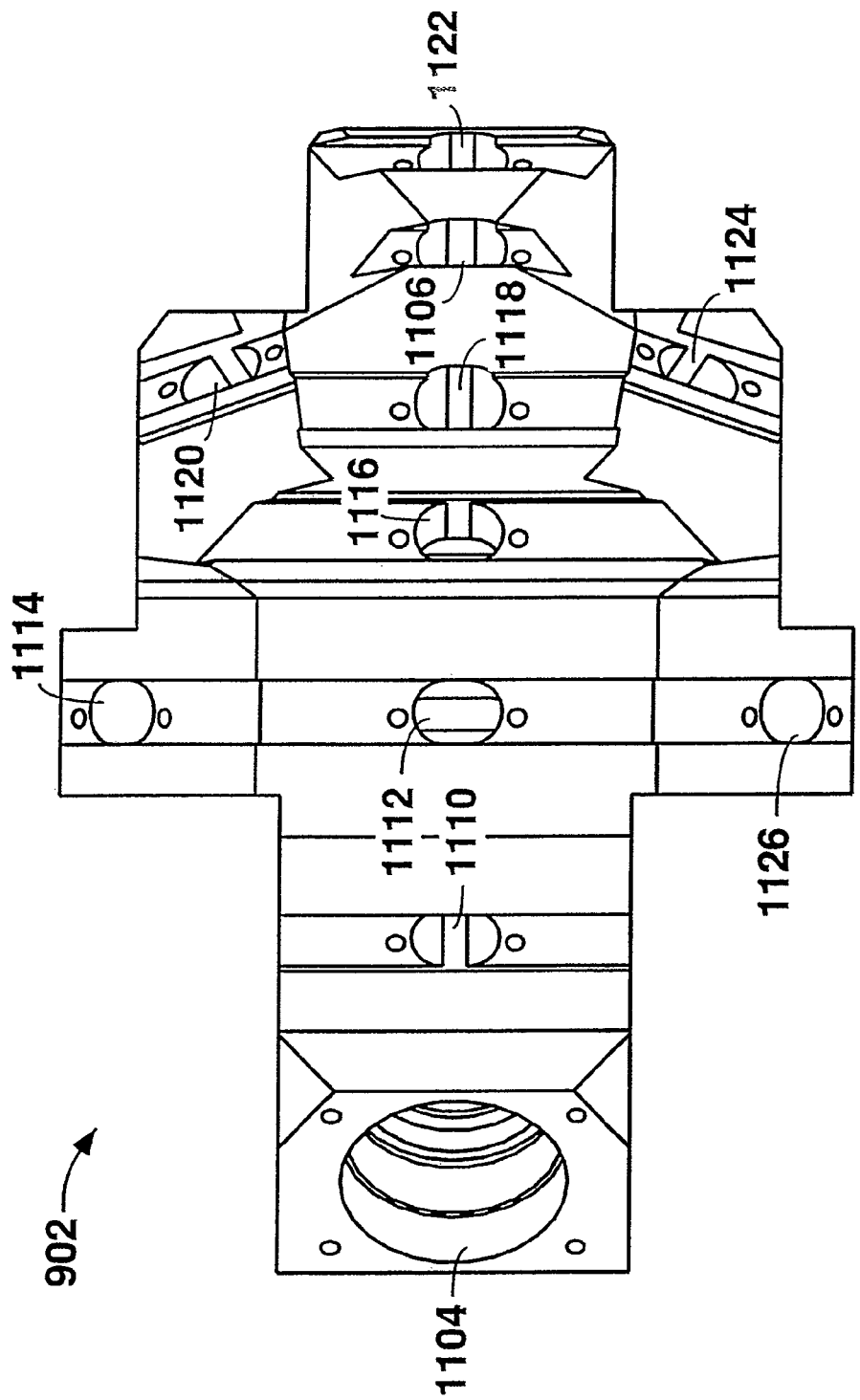
Figure 13:
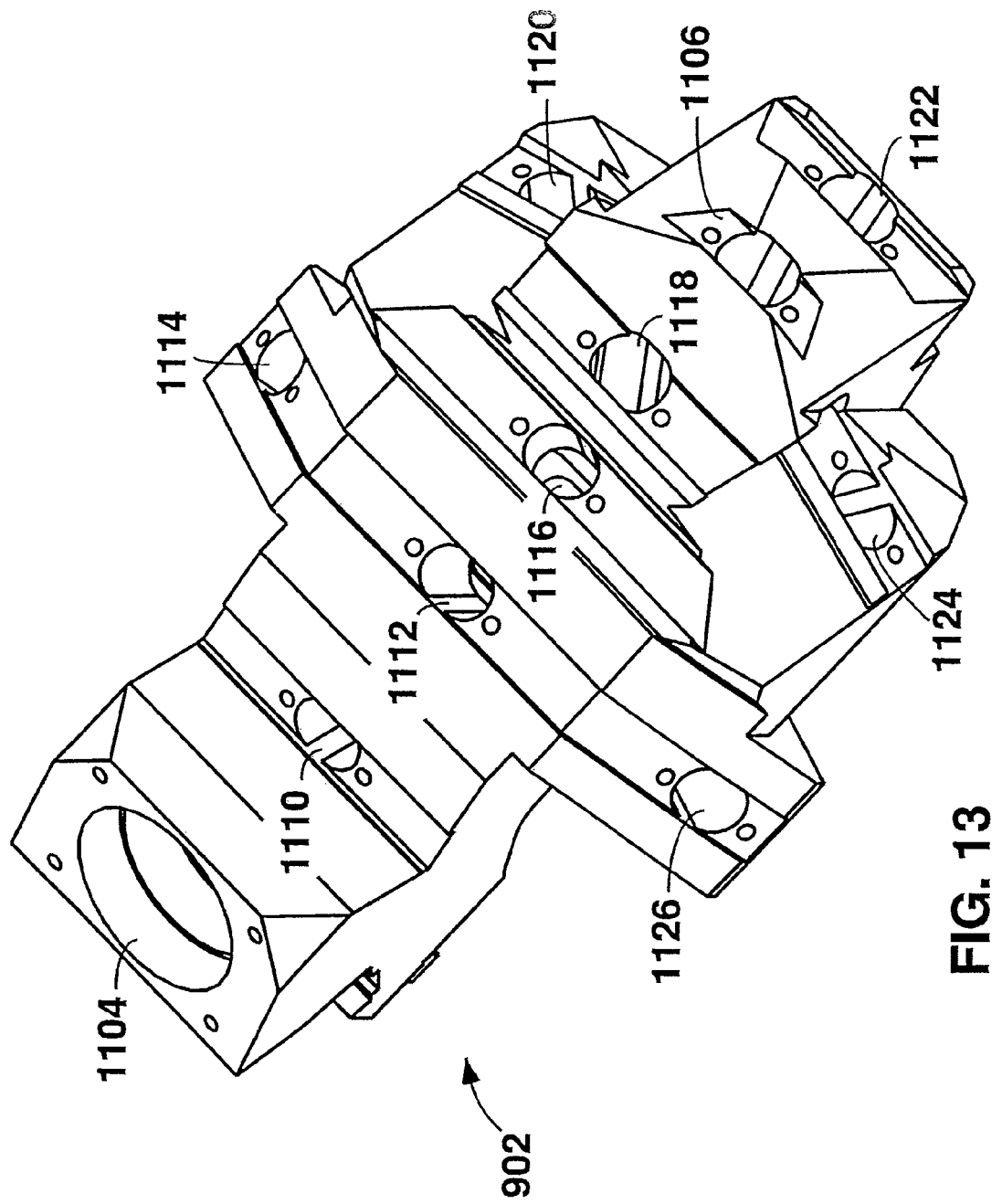
Figure 14:
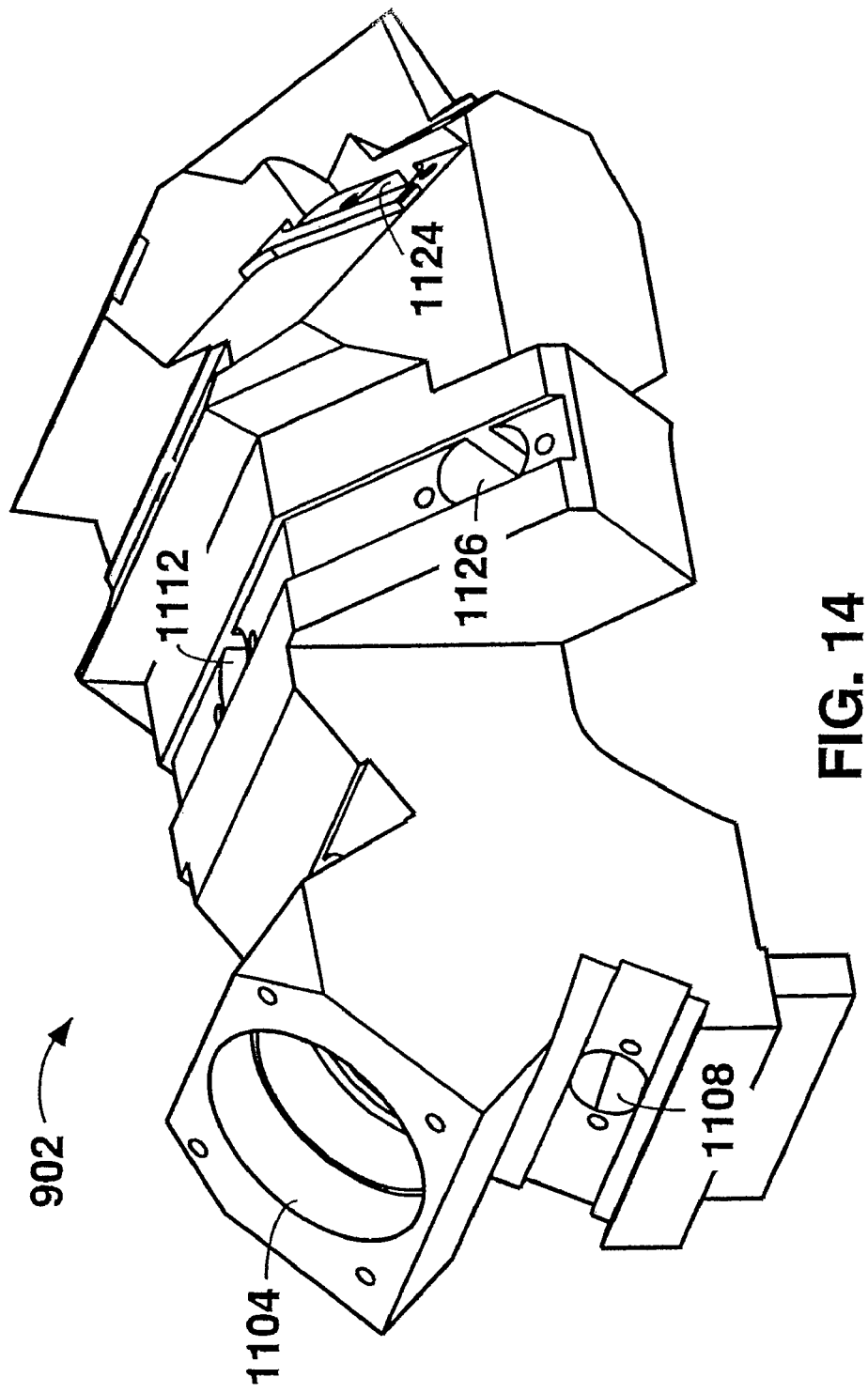

FIG. 10 shows an exemplary database schema 1000 that may be used to store measurement data, for example, at database 924 and/or electronics unit 904. Box 1002 may include information about the instrument (e.g., instrument 900) that is taking the measurement. Such information can include a name, serial number, etc. Box 1004 may include information about a particular measurement including, for example, date, time, location number, instrument orientation, etc. Boxes 1006 and 1008 may include information about the panel or surface under measurement. For example, box 1006 may include information about the panel or surface itself while box 1008 may include a template of preferred measurements to be taken on the surface (e.g., the number, height, width, distance from the edge, etc.). Box 1010 may include information about each of the angles or reflectance directions that are to be observed, and box 1012 may include actual measured data. For example, if eleven reflectance directions are measured over thirty-one wavelength ranges, then the total number of data points for each measurement may be 341.

FIGS. 11-14 show views of an exemplary optics unit 902 according to various embodiments. The exemplary optics unit 902 includes one illumination source 1104 and eleven apertures or pupils for receiving sensors 1106, 1108, 1110, 1112, 1114, 1116, 1118, 1120, 1122, 1124, 1126. It will be appreciated that sensor may comprise an aperture for receiving light and a receiving element for sensing the intensity of the light. In the exemplary unit 902, the illumination source 1104 is directed toward a surface positioned below the unit (not shown) at a forty-five degree angle relative to the surface normal. Accordingly, the specular reflectance direction is also at a forty-five degree angle relative to the surface normal. Pupil 1106 may be positioned to sense reflectance at the specular reflectance direction.

In various embodiments, the positions of the other pupils may be expressed relative to the specular reflectance direction, although, it will be appreciated that the positions of the pupils may be expressed in any suitable coordinate system. For example, pupil 1122 may be positioned at −15° relative to the specular. Pupil 1118 may be at 15° relative to the specular, with pupil 1116 at 25°, pupil 1112 at 45°, pupil 1110 at 75°, and pupil 1108 at 110°. The location of pupils off the plane of pupils 1106, 1108, 1110, 1112, 1116, and 1118 may also be expressed relative to the specular reflectance direction. For example, pupil 1124 is positioned 25° from the specular reflectance direction and rotated 90° counterclockwise out of plane. Similarly, pupil 1120 is positioned 25° from the specular reflectance direction and rotated 90° clockwise out of plane. Pupils 1114 and 1126 are both positioned 60° from the specular reflectance direction and rotated 54.7° clockwise and counterclockwise out of plane, respectively.

Figure 15:
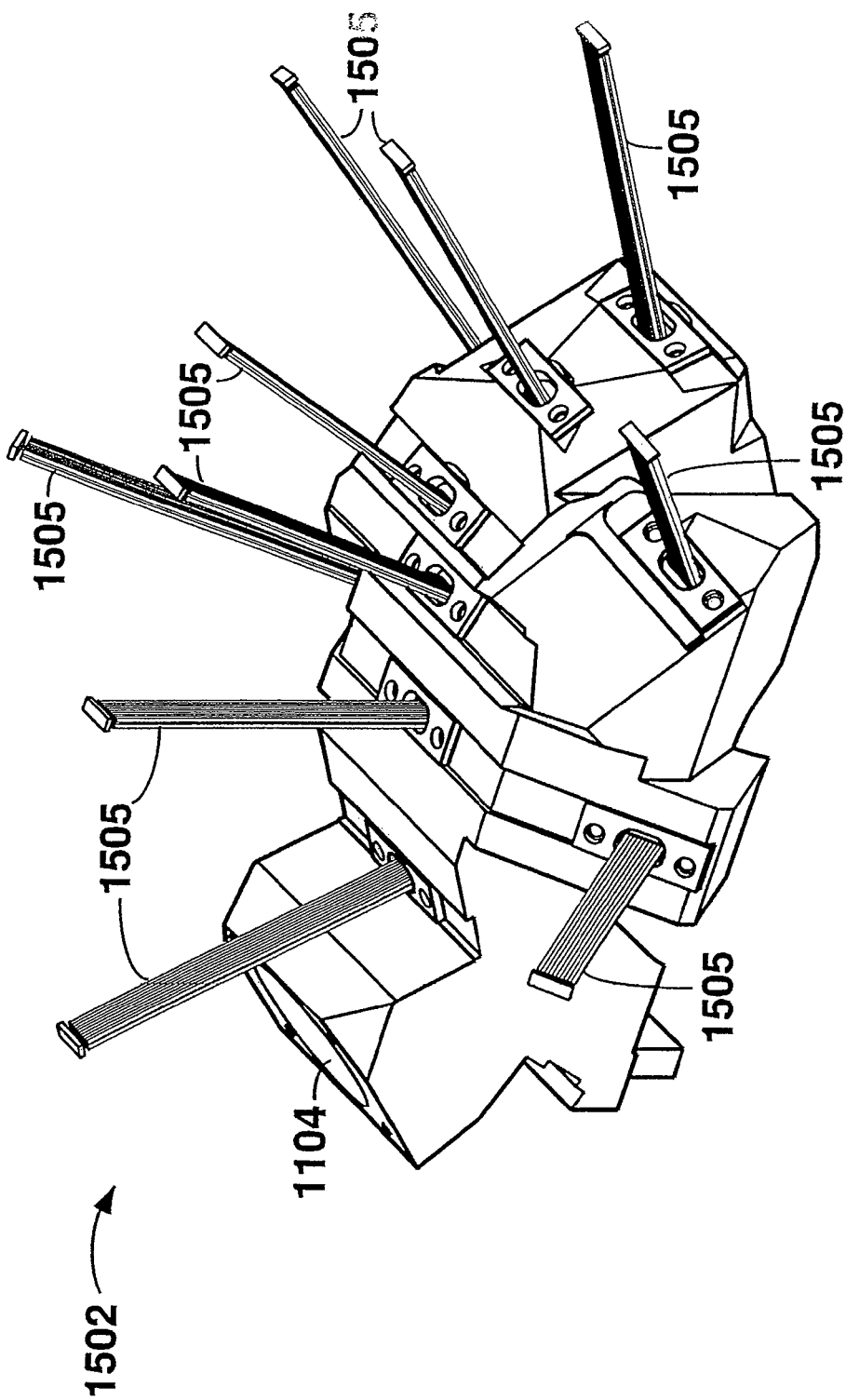
FIG. 15 shows a three-dimensional view of an apparatus according to various embodiments of the present invention.

It will be appreciated that although eleven pupils for sensors are shown, any suitable number of sensors may be used. Also the sensors may be placed to receive any suitable reflectance directions, for example, reflectance directions that are non-coplanar. Also, in various embodiments, the sensors may be positioned at in the various pupils of the optics unit 902. In other various embodiments, some or all of the sensors may be positioned remote from the pupils. For example, FIG. 15 shows another exemplary optics unit 1502 having optical fibers 1505 originating at various pupils. The fibers 1505 may transport light incident at the pupils to a remote location (not shown) that may house one or more receiving elements.

Figures 17, 18:
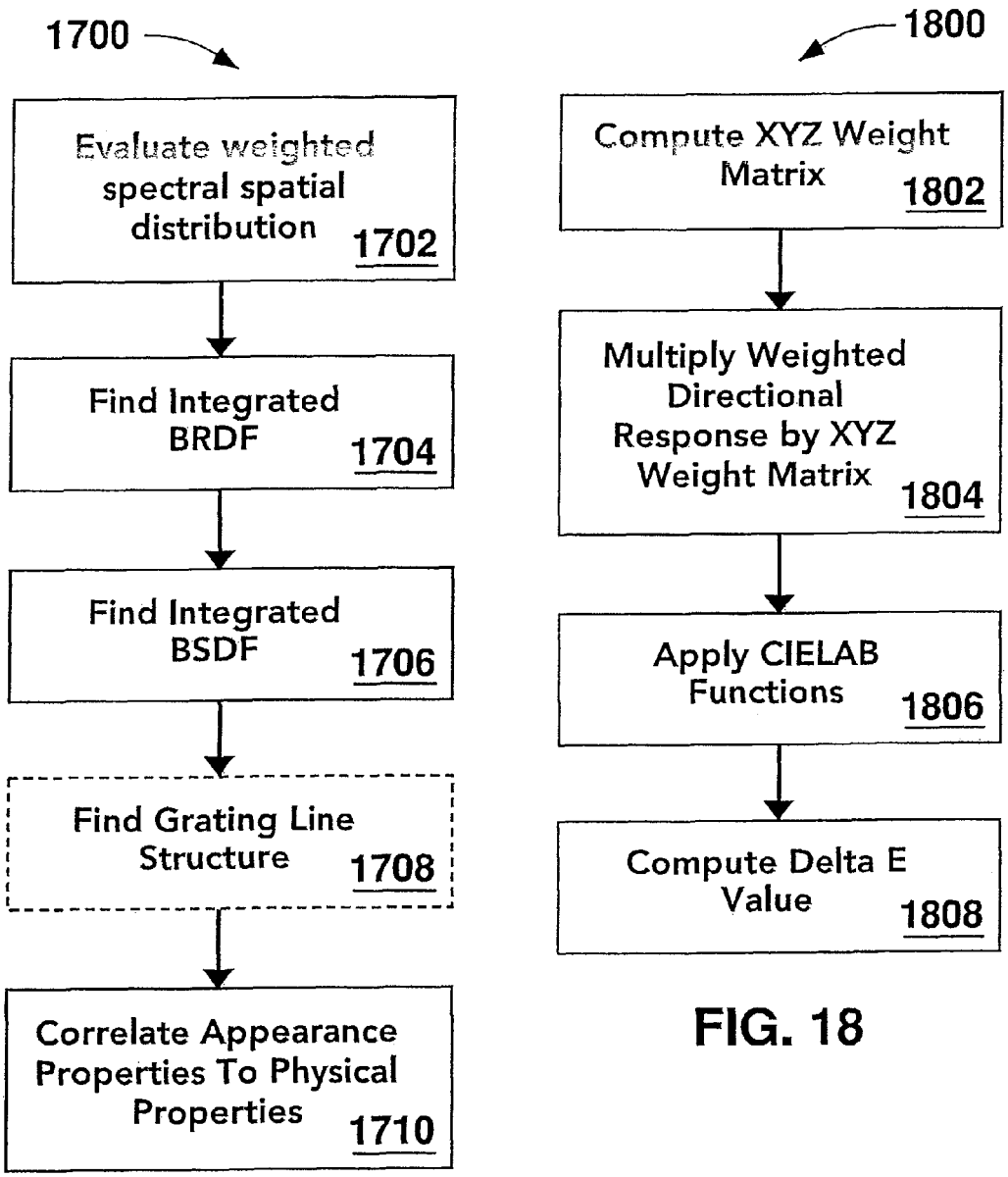

FIG. 17 shows an exemplary process flow 1700 for identifying properties of an unknown surface using the methods and/or apparatuses described above. At steps 1702, 1704, 1706, and 1708, various appearance properties may be derived from the observed reflectance or BRDF of the surface. For example, at step 1704, a magnitude of the weighted spectral spatial distribution may be found. At step 1704, an integrated BRDF of the surface may be found. An integrated BSDF of the surface may be found at step 1706. In various embodiments, a grating line structure of the surface may be found at step 1708. At step 1710, the appearance properties are compared to a look-up table, such as look-up Table 1, below to identify the unknown surface and/or physical properties thereof. It will be appreciated that the look-up table may be stored, for example, by the database 924 and/or the electronics unit 904 of the device 900.

TABLE 1

| Surface Type\Properties | Weighted Spectral Spatial Distribution Magnitude | Integrated BRDF | Integrated BSDF | Grating Structure Line | Moment Size | Diffuse/Specular |
|---|---|---|---|---|---|---|
| Specular Absorber | Small | Small | Small | N/A | N/A | Specular |
| Pigmented Surface | Small | Small | Large | N/A | Medium | N/A |
| Surface Texture Absorber | Small | Small | Large | N/A | Small | N/A |
| Specular Pure Absorber | Small | Large | Small | N/A | N/A | N/A |
| Heavy Surface Structure | Large | Small | Small | Yes | N/A | N/A |
| Metal Flake | Large | Small | Large | No | N/A | N/A |
| Special Effect - Chroma Flair | Large | Small | Large | Yes | N/A | N/A |
| Special Effect - Mica | Large | Large | Small | No | N/A | N/A |
| Surface Scratches | Large | Large | Small | Yes | N/A | N/A |
| Special Effect - Chroma Flair | Large | Large | Large | Yes | N/A | N/A |
| Potential Calibration Error | Large | Large | Large | No | N/A | N/A |
| Potential Calibration Error | Small | Small | Small | N/A | N/A | Diffuse |
| Potential Calibration Error | Small | Large | Large | N/A | N/A | N/A |
| Undetermined | Large | Small | Small | No | N/A | N/A |

FIG. 18 shows a process flow 1800 for using the processes and/or apparatuses described above to find a directional color difference between two surfaces according to various embodiments. In the process flow 1800, the directional color difference is a Delta E value computed according to the CIELAB equations, though it will be appreciated that any suitable color measurement methodology may be used. At step 1802, an XYZ weight matrix may be computed based on a specified illuminant and observer. The XYZ weight matrix may be of size 3 by X, where X is the number of discrete wavelengths or wavelength range that are measured. Recall that the weighted directional response can be represented by a set of vectors, with one vector for each wavelength range. Accordingly, the weighted directional response may be represented as a vector of size X by d, where d is the number of terms necessary to represent the spatial coordinate axis (e.g., in three dimensions, d is equal to 3). The two matrices may be multiplied at step 1804 resulting in a 3 by d matrix. The CIELAB functions may be applied at step 1806. In various embodiments, the CIELAB functions may be applied to each column of the 3 by d matrix individually. Alternatively, the CIELAB functions may be applied to the magnitude of each column of the 3 by d matrix. At step 1808, the Delta E value may be calculated.

FIG. 19 shows a process flow 1900 that may be utilized in the coatings industry, for example, by a finisher of automotive parts, to match the appearance of coatings applied to two components, which may be manufactured and coated at different times and different facilities (e.g., a door handle may be made at Factory A, while a bumper may be made at Factory B). The process flow 1900 may be used to determine coating formulation and/or process factors for the second component based on observations of the first component. At step 1902, an appearance property of a first coated component may be measured and/or calculated. The appearance property may be, for example, a weighted directional response, BRDF, etc. At step 1904, an appearance property of a second coated component may be measured, for example in the same way as the first. At step 1906, the appearance properties of the two coated components may be compared. If differences are found, (e.g., because the second coated component does not match the first) then the appearance property exhibiting the differences may be tied to a particular formulation or application factor at step 1908, for example, as described above. The formulation or application factor of the second coated component may then be modified, at step 1910, to coat additional components to match the first, allowing a higher quality appearance match between components.

FIG. 20 shows a process flow 2000 for determining process and/or formulation factors to be used when coating a replacement part. At step 2002, an appearance property of a first coated component may be found (e.g., a weighted directional response, BRDF, etc.). The first coated component may be, for example, a component of an automobile. At step 2004, a formulation or application factor for reproducing the appearance of the coating on the first component may be found (e.g., by tying the appearance property to the formulation or application factor). At step 2006, a coating may be applied to a second component, considering the formulation or application factor found at step 2004. The process flow 2000 may be useful, for example, to autobody shops. In this way the coating of the second component may match that of the first. Using the process flow 2000, an autobody shop may match the paint formulation and process used to repaint a component or paint a replacement component to match the appearance of components already on the car. This may provide a better appearance match then reproducing the original formulation and process factors, as the appearance of the components changes with weathering and wear.

Figures 21, 22:
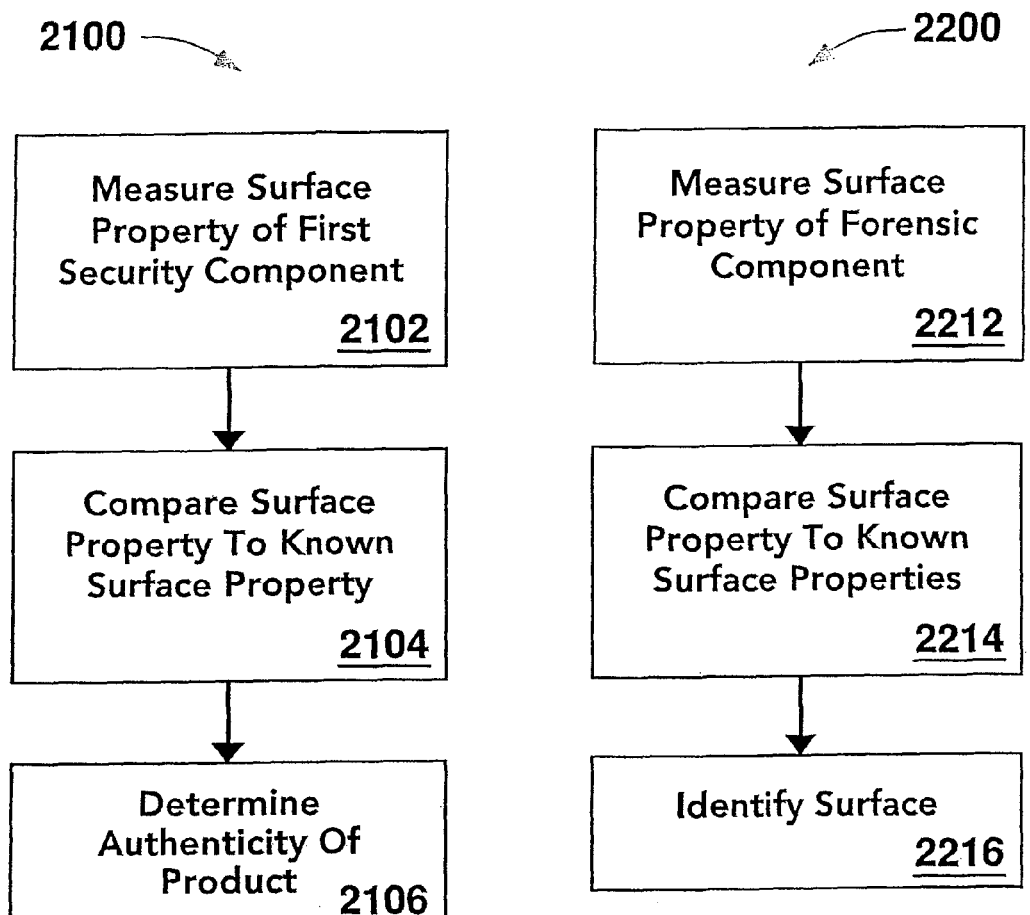

FIG. 21 shows a process flow 2100, according to various embodiments, for verifying the identity of a security component. The security component may be, for example, a security ink (e.g., a security ink having an appearance that depends on viewing angle). The ink may be present on a label or other indicator on a product. In various embodiments, the security component may be the product itself, for example, in the instance of a cosmetic or similar product having a distinct appearance. Referring to the process flow 2100, at step 2102, an appearance property of the first unknown component may be measured. The appearance property may be a weighted directional response, BDRF, etc. At step 2104, the measured appearance property may be compared to a known appearance property of an authentic security component. The authenticity of the product under test may be found at step 2106. For example, if the appearance property of the unknown security component matches the appearance property of the known product, then the unknown product is likely authentic. If the property of the tested security component does not match the known property, then the product may be counterfeit. It will be appreciated that the reliability of the match may be increased by considering multiple independent appearance properties.

FIG. 22 shows a process flow 2200 according to various embodiments, for identifying the source of a component. The process flow 2200 may be useful, for example, to forensic investigations. At step 2212, an appearance property of a component may be analyzed. The component may be, for example, an automobile body piece at the scene of a hit and run accident, a scrap of clothing left at the scene of a crime, or other component that is the subject of a forensic investigation. At step 2214, the appearance property of the component may be compared to similar properties of components of known origins. At step 2216, the component may be identified based on a match between the measured appearance property and the known appearance properties. For example, an automobile body piece may be tied to a particular make, model, production run, etc.

It is to be understood that the figures and descriptions of the present invention have been simplified to illustrate elements that are relevant for a clear understanding of the present invention, while eliminating, for purposes of clarity, other elements, such as, for example, some specific tasks of the non-execution service provider units described above, etc. Those of ordinary skill in the art will recognize that these and other elements may be desirable. However, because such elements are well known in the art and because they do not facilitate a better understanding of the present invention, a discussion of such elements is not provided herein.

As used herein, a "computer" or "computer system" may be, for example and without limitation, either alone or in combination, a personal computer (PC), server-based computer, main frame, server, microcomputer, minicomputer, laptop, personal data assistant (PDA), cellular phone, pager, processor, including wireless and/or wireline varieties thereof, and/or any other computerized device capable of configuration for processing data for standalone application and/or over a networked medium or media. Computers and computer systems disclosed herein may include operatively associated memory for storing certain software applications used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, ROM (read only memory), RAM (random access memory), PROM (programmable ROM), EEPROM (extended erasable PROM), and/or other like computer-readable media.

The various modules 916, 918 of the system 901 may be implemented as software code to be executed by a processor(s) of the system 901 or any other computer system using any type of suitable computer instruction type. The software code may be stored as a series of instructions or commands on a computer readable medium. The term "computer-readable medium" as used herein may include, for example, magnetic and optical memory devices such as diskettes, compact discs of both read-only and writeable varieties, optical disk drives, and hard disk drives. A computer-readable medium may also include memory storage that can be physical, virtual, permanent, temporary, semi-permanent and/or semi-temporary. A computer-readable medium may further include one or more data signals transmitted on one or more carrier waves.

While several embodiments of the invention have been described, it should be apparent that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

We claim:

1. An apparatus for measuring a spatially under-sampled Bidirectional Reflectance Distribution Function (BRDF) of a surface, the apparatus comprising:
a first light source directed to illuminate the surface from a first illumination direction;
a plurality of sensors positioned to receive light reflected by the surface, wherein the plurality of sensors comprises:
a first sensor positioned to receive light reflected by the surface in a first reflectance direction;
a second sensor positioned to receive light reflected by the surface in a second reflectance direction; and
a third sensor positioned to receive light reflected by the surface in a third reflectance direction, wherein the first, second, and third directions are not coplanar; and
a computer in communication with the plurality of sensors, wherein the computer is configured to convert light sensed by the plurality of sensors into a first appearance property of the surface considering the first, second, and third reflectance directions,
wherein the first appearance property includes a plurality of directional responses of the surface,
wherein each directional response is for a different wavelength or range of wavelengths,
wherein the plurality of directional responses comprises a set of vectors,
and wherein each of the set of vectors represents a vector sum of light measured over the plurality of reflectance directions at a given wavelength or wavelength range.

2. The apparatus of claim 1, further comprising a second light source incident on the surface at a second illumination angle.

3. The apparatus of claim 1, wherein the plurality of sensors further comprises a fourth sensor positioned to receive light reflected by the surface at a fourth reflectance angle.

4. The apparatus of claim 1, wherein the plurality of sensors comprises between 5 and fifteen sensors.

5. The apparatus of claim 1, wherein the first sensor is sensitive to a plurality of discrete wavelength ranges.

6. The apparatus of claim 1, wherein the first, second, and third reflectance directions are orthogonal to the first illumination direction relative to a surface normal of the surface.

7. The apparatus of claim 1, wherein the plurality of sensors includes sensors positioned at aspecular angles of 15, 25, 45, 75, and 110 degrees.

8. The apparatus of claim 1, wherein the plurality of sensors include a sensor at an aspecular angle of −15 degrees.

9. The apparatus of claim 1, wherein the first light source is a collimated beam source.

10. The apparatus of claim 1, wherein the first light source comprises a white Light Emitting Diode (LED).

11. The apparatus of claim 1, wherein the first light source comprises an incandescent light bulb.

12. The apparatus of claim 1, wherein the first illumination direction forms an angle with the surface normal of zero degrees.

13. The apparatus of claim 1, wherein the first illumination direction forms an angle with the surface normal of greater than forty five degrees.

14. The apparatus of claim 1, wherein the plurality of sensors includes a non-imaging sensor.

15. The apparatus of claim 1, wherein the first sensor comprises a photodiode and at least one spectral band pass filter positioned between the reflected light and the photodiode.

16. The apparatus of claim 1, wherein the first sensor comprises a wide band spectral detector.

17. The apparatus of claim 1, wherein the first light source comprises a plurality of LED's having different spectral outputs.

18. The apparatus of claim 1, wherein the first sensor comprises a receiving element and a first pupil directed to receive the light reflected in the first reflectance direction, wherein the first pupil is positioned between the surface and the receiving element.

19. The apparatus of claim 15, wherein the spectral band pass filter is part of a color wheel positioned between the reflected light and the photodiode.

20. The apparatus of claim 16, wherein the wide band spectral detector is a RGB sensor.

21. The apparatus of claim 17, wherein the plurality comprises nine LED, and wherein each of the nine LED's has a different spectral output.

22. The apparatus of claim 18, wherein the first pupil is optically connected to the receiving element with at least one fiber optic cable.

23. The apparatus of claim 18, further comprising at least one lens positioned between an aperture and the receiving element.

24. A method for measuring a spatially under-sampled Bidirectional Reflectance Distribution Function (BRDF) of a surface, the method comprising:
    illuminating the surface with a first light source incident on the surface from a first illumination direction;
    sensing light of a plurality of wavelengths reflected by the surface in a plurality of reflectance directions, wherein the plurality of reflectance directions comprises a first reflectance direction, a second reflectance direction and a third reflectance direction; and
    converting the sensed light into a first appearance property of the surface considering the first, second, and third reflectance directions,
    wherein the first appearance property includes a plurality of directional responses of the surface,
    wherein each directional response is for a different wavelength or range of wavelengths,
    wherein the plurality of directional responses comprises a set of vectors,
    and wherein each of the set of vectors represents a vector sum of light measured over the plurality of reflectance directions at a given wavelength or wavelength range.

25. The method of claim 24, further comprising illuminating the surface with a second light source incident on the surface from a second illumination direction.

26. The method of claim 24, wherein the plurality of reflectance directions further comprises a fourth reflectance direction.

27. The method of claim 24, wherein the plurality of reflectance directions comprises between five and fifteen reflectance directions.

28. The method of claim 24, further comprising calculating a mean spectral spatial moment, wherein the mean spectral spatial moment is the average direction of the directional responses.

29. The method of claim 24, further comprising calculating a spectral spatial distribution, wherein the spectral spatial distribution is a function representing a line shape of end points of the set of vectors included in the directional responses.

30. The method of claim 24, further comprising calculating a Delta E value between the surface and a second surface.

31. The method of claim 24, further comprising converting the sensed light into a second appearance property of the surface wherein the second appearance property is a grating structure period.

32. The method of claim 24, further comprising converting the sensed light into a second appearance property of the surface wherein the second appearance property is an index of refraction.

33. The method of claim 24, wherein the first appearance property of the surface represents a property of a formulation of a coating present on the surface.

34. The method of claim 24, wherein the first appearance property of the surface represents a property of a process used to apply a coating present on the surface.

35. The method of claim 24, wherein the sensing light comprises sensing light utilizing at least one sensor in a fixed position.

36. The method of claim 24, wherein the sensing light comprises sensing light with at least one non-imaging sensor.

37. The method of claim 24, wherein the first, second and third reflectance directions are non-coplanar.

38. The method of claim 24, further comprising transforming the plurality of directional responses of the surface based on directional responses of a standard surface.

39. The method of claim 24, further comprising applying a weighting factor for each reflectance direction in the vector sum.

40. The method of claim 24, wherein a number of the plurality of reflectance directions is related to a physical property of the surface.

41. The method of claim 24, wherein the first appearance property is the spatially under-sampled BRDF of the surface.

42. The method of claim 38, wherein the calculating comprises applying CIELAB equations to the plurality of directional responses.

43. The method of claim 39, wherein the weighting factor is determined based on an expected distribution of energy reflected by the surface.

44. The method of claim 40, wherein the number of the plurality of reflectance directions is equal to:

$$2L+m$$

wherein L is equal to the number of layers present on the surface and m is equal to the number of different materials included in the surface.

45. The method of claim 40, wherein the number of the plurality of reflectance directions is equal to:

$$6L+6m$$

wherein L is equal to the number of layers present on the surface and m is equal to the number of different materials included in the surface.

46. The method of claim 41, further comprising calculating an approximation of a Bidirectional Scatter Distribution Function (BSDF) by subtracting a specular component from the spatially under-sampled BRDF.

47. The method of claim 46, further comprising calculating a term proportional to topographic scattering by the surface by dividing the approximation of the BSDF by a topographic scattering factor.

48. The method of claim 46, further comprising calculating a term proportional to material scattering by the surface by dividing the approximation of the BSDF by a material scattering factor.

49. The method of claim 46, further comprising calculating a term proportional to defect scattering by the surface by dividing the approximation of the BSDF by a defect scattering factor.

50. A system for measuring a spatially under-sampled Bidirectional Reflectance Distribution Function (BRDF) of a surface, the system comprising:
 illumination optics configured to illuminate the surface with at least one light source;
 receiving optics configured to sense light of a plurality of wavelengths reflected from the surface in a plurality of reflectance directions, wherein the plurality of reflectance directions comprises first, second, and third reflectance directions; and
 a processing module configured to convert light sensed by the receiving optics into a first appearance property of the surface considering the first, second, and third reflectance directions,
 wherein the first appearance property includes a plurality of directional responses of the surface,
 wherein each directional response is for a different wavelength or range of wavelengths,
 wherein the plurality of directional responses comprises a set of vectors,
 and wherein each of the set of vectors represents a vector sum of light measured over the plurality of reflectance directions at a given wavelength or wavelength range.

51. The system of claim 50, wherein the illumination optics, receiving optics and processing module are contained in a single enclosure.

52. The system of claim 50, wherein the processing module is remote from the illumination optics and receiving optics.

53. The system of claim 50, wherein the receiving optics comprise at least two sensors at fixed locations.

54. The system of claim 50, wherein the receiving optics comprises at least one non-imaging sensor.

55. The system of claim 54, wherein the first, second and third reflectance directions are non-coplanar.

56. A method for matching the appearance of coatings applied to a first component and a second component, the method comprising:
 finding a first appearance property of the first component, wherein finding the first appearance property comprises:
  illuminating a surface of the first component with a first light source incident on the surface from a first illumination direction; and
  sensing light of a plurality of wavelengths reflected by the surface in a plurality of reflectance directions, wherein the plurality of reflectance directions comprises first, second and third reflectance directions, and wherein the first appearance property considers the first, second, and third reflectance directions, wherein the first appearance property includes a plurality of directional responses of the surface, wherein each directional response is for a different wavelength or range of wavelengths, wherein the plurality of directional responses comprises a set of vectors, and wherein each of the set of vectors represents a vector sum of light measured over the plurality of reflectance directions at a given wavelength or wavelength range;
 finding a second appearance property of the second component;
 comparing the first and the second appearance properties; and
 relating a difference between the first and second appearance properties to a coating factor.

57. The method of claim 56, wherein the coating factor comprises at least one of a formulation and an application factor.

58. The method of claim 56, wherein the first appearance property includes a weighted directional response.

59. The method of claim 56, further comprising coating a third component type considering the coating factor.

60. The method of claim 56, wherein the sensing light comprises sensing light utilizing at least one sensor in a fixed position.

61. The method of claim 56, wherein the sensing light comprises sensing light with at least one non-imaging sensor.

62. The method of claim 56, wherein the first, second and third reflectance directions are non-coplanar.

63. A method of repairing a device, the method comprising:
 finding a first appearance property of a first component of the device, wherein finding the first appearance property comprises:
  illuminating a surface of the first component with a first light source incident on the surface from a first illumination direction; and
  sensing light of a plurality of wavelengths reflected by the surface in a plurality of reflectance directions, wherein the plurality of reflectance directions comprises first, second and third reflectance directions, and wherein the first appearance property considers the first, second, and third reflectance directions, wherein the first appearance property includes a plurality of directional responses of the surface, wherein each directional response is for a different wavelength or range of wavelengths, wherein the plurality of directional responses comprises a set of vectors, and wherein each of the set of vectors represents a vector sum of light measured over the plurality of reflectance directions at a given wavelength or wavelength range;
 relating the first appearance property to a coating factor of the first component; and
 coating a replacement component of the device considering the coating factor.

64. The method of claim 63, wherein the coating factor comprises at least one of a formulation and an application factor.

65. The method of claim 63, wherein the appearance property includes a weighted directional response.

66. The method of claim 63, wherein the device is a car.

67. The method of claim 63, wherein the sensing light of a plurality of wavelengths in a plurality of reflectance directions comprises sensing light utilizing at least one sensor in a fixed position.

68. The method of claim 63, wherein the sensing light comprises sensing light with at least one non-imaging sensor.

69. The method of claim 63, wherein the first, second and third reference directions are non-coplanar.

70. A method of finding the identity of an unknown object, the method comprising:
 finding a first appearance property of the object, wherein finding the first appearance property comprises:

illuminating a surface of the object with a first light source incident on the surface from a first illumination direction; and sensing light of a plurality of wavelengths reflected by the surface in a plurality of reflectance directions, wherein the plurality of reflectance directions comprises first, second and third reflectance directions, and wherein the first appearance property considers the first, second, and third reflectance directions, wherein the first appearance property includes a plurality of directional responses of the surface, wherein each directional response is for a different wavelength or range of wavelengths, wherein the plurality of directional responses comprises a set of vectors, and wherein each of the set of vectors represents a vector sum of light measured over the plurality of reflectance directions at a given wavelength or wavelength range; and comparing the first appearance property to an appearance property of a known object.

71. The method of claim 70, wherein the appearance property includes-a weighted directional response.

72. The method of claim 70, further comprising determining the authenticity of the object based on the comparing.

73. The method of claim 70, further comprising identifying a source of the object based on the comparison.

74. The method of claim 70, wherein the sensing light of a plurality of wavelengths in a plurality of reflectance directions comprises sensing light utilizing at least one sensor in a fixed position.

75. The method of claim 70, wherein the sensing light comprises sensing light with at least one non-imaging sensor.

76. The method of claim 70, wherein the first, second and third reference directions are non-coplanar.

* * * * *